(12) United States Patent
Sundermann et al.

(10) Patent No.: US 7,230,018 B2
(45) Date of Patent: Jun. 12, 2007

(54) SUBSTITUTED PROPANE-1,3-DIAMINE DERIVATIVES AND THE PHARMACEUTICAL USE THEREOF

(75) Inventors: Bernd Sundermann, Aachen (DE); Helmut Buschmann, Esplugues de Llobregat (ES); Babette-Yvonne Koegel, Langerwehe-Hamich (DE); Beatrix Merla, Aachen (DE); Nikolaus Risch, Lemgo (DE)

(73) Assignee: Gruenenthal GmbH, Aachen (DE)

( * ) Notice: Subject to any disclaimer, the term of this patent is extended or adjusted under 35 U.S.C. 154(b) by 336 days.

(21) Appl. No.: 10/644,981

(22) Filed: Aug. 21, 2003

(65) Prior Publication Data

US 2004/0067928 A1    Apr. 8, 2004

Related U.S. Application Data

(63) Continuation of application No. PCT/EP02/01765, filed on Feb. 20, 2002.

(30) Foreign Application Priority Data

Feb. 21, 2001   (DE)   ................................. 101 08 307

(51) Int. Cl.
   *A61K 31/44*   (2006.01)
   *C07D 213/38*   (2006.01)

(52) U.S. Cl. ...................... 514/357; 546/333; 564/306; 564/192; 564/183; 514/649; 514/625; 514/617

(58) Field of Classification Search ................ 514/357, 514/617, 625, 649; 546/333, 183, 192, 306; 564/306

See application file for complete search history.

(56) References Cited

U.S. PATENT DOCUMENTS 4,017,637 A    4/1977   Yardley et al. .............. 424/311

6,288,278 B1   9/2001   Sundermann et al. ....... 564/391
6,410,790 B1   6/2002   Sundermann et al. ....... 564/336

FOREIGN PATENT DOCUMENTS

EP   1043306   10/2000
EP   1043307   10/2000

OTHER PUBLICATIONS

Merla, B. et al.: Efficient synthesis of Diastereomerically pure 1,3-diamines. Synthesis, vol. 10, pp. 1365-1372, 2002.*
Arend, M. et al., "A Simple And Highly Diastereoselective One-Pot Synthesis Of Mannich-Bases" *Synlett*, (1997) pp. 974-976.
Cannarsa, M., "Single enantiomer drugs: new strategies and directions", *Chemistry & Industry*, May 20, 1996, pp. 374-378.
Carlson, R. et al., "Improved Titanium Tetrachloride Procedure for Enamine Synthesis. II.*Scope of the Reaction", *Acta Chem. Scand.* B 38 (1984) pp. 49-53.
J. March, "Advanced Organic Chemistry" Third Edition, (1985) pp. 796-800.
Masamune, S. et al., "Aldol Methodology" Synthesis of Versatile Intermediates. 3-Hydroxy-2-vinylcarbonyl Compounds *J. Am. Chem. Soc.* 1982, 104, pp. 5521-5523.
Merla, B. et al., "A Simple and Highly Diastereoselective One-Pot Synthesis of 1,3-Diamines" *Synlett*, (1997) pp. 177-178.
Mitsunobu, O., "The Use of Diethyl Azodicarboxylate and Triphenylphosphine in Synthesis and Transformation of Natural Products" *Synthesis*, Jan. 1981, pp. 1-28.
Risch, N. et al., "Simple Diastereoselection" *Houben-Weyl*, vol. E21b (1995) pp. 1925-1929.
Risch, N. et al., "Diastereomerenreine Mannich-Basen durch Addition von Enaminen an ternaere Iminiumsalze" *Angew. Chem.* 106 (1994) 2531-2533.
Tschaen, D. et al., "Asymmetric Synthesis of MK-0499" *J. Org. Chem.* 1995, 60, 4324-4330.

* cited by examiner

*Primary Examiner*—Charanjit S. Aulakh
(74) *Attorney, Agent, or Firm*—Crowell & Moring LLP

(57) ABSTRACT

Substituted propane-1,3-diamine derivatives, methods for producing such derivatives, and medicaments and pharmaceutical compositions containing such derivatives useful for the treatment or prophylaxis of pain, urinary incontinence, itching, tinitus aurium, or diarrhea are provided.

35 Claims, No Drawings

SUBSTITUTED PROPANE-1,3-DIAMINE DERIVATIVES AND THE PHARMACEUTICAL USE THEREOF

CROSS REFERENCE TO RELATED APPLICATIONS

This application is a continuation of International Patent Application No. PCT/EP02/01765, filed Feb. 20, 2002, designating the United States of America, and published in German as WO 02/66432, the entire disclosure of which is incorporated herein by reference. Priority is claimed based on Federal Republic of Germany Patent Application No. DE 101 08 307.6, filed Feb. 21, 2001.

FIELD OF THE INVENTION

The present invention relates to substituted propane-1,3-diamine derivatives, processes for their preparation, medicaments and pharmaceutical compositions comprising them and their use for the preparation of medicaments for treatment and/or prophylaxis of pain, urinary incontinence, itching, tinnitus aurium and/or diarrhoea.

BACKGROUND OF THE INVENTION

Treatment of chronic and non-chronic states of pain is of great importance in medicine. There is a world-wide need for pain therapies which have a good action for target-orientated treatment of chronic and non-chronic states of pain appropriate for the patient, by which is to be understood successful and satisfactory pain treatment for the patient.

Conventional opioids, such as morphine, have a good action in the treatment of severe to very severe pain. However, their use is limited by the known side effects, such as e.g. respiratory depression, vomiting, sedation, constipation and development of tolerance. Furthermore, they are less active on neuropathic or incidental pain, from which tumour patients suffer in particular.

SUMMARY OF INVENTION

The object of the present invention was therefore to provide compounds which have an analgesic action and are suitable for pain treatment—in particular also for treatment of chronic and neuropathic pain. These substances should moreover as far as possible have none of the side effects which conventionally occur when opioids with a μ-receptor affinity, such as morphine, are used, such as e.g. nausea, vomiting, dependency, respiratory depression or constipation.

This object is achieved by the compounds of the general structure (I), which have an analgesic action. The compounds according to the invention are substituted 1,3-propane-diamine derivatives of the general structure (I) and their pharmaceutically acceptable salts

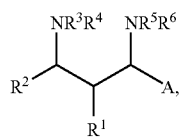

I wherein $R^1$ denotes $C_{1-12}$-alkyl, $C_{3-8}$-cycloalkyl, —($C_{1-6}$-alkyl)-$C_{3-8}$- cycloalkyl or aryl, $R^2$ denotes $C_{1-12}$-alkyl, $C_{3-8}$-cycloalkyl, —($C_{1-6}$-alkyl)-$C_{3-8}$- cycloalkyl, aryl, —($C_{1-6}$-alkyl)-aryl, heterocyclyl or —($C_{1-6}$-alkyl)-heterocyclyl, wherein $R^1$ and $R^2$ are not at the same time aryl or aryl and heterocyclyl, or $R^1$ and $R^2$ together form —$(CH_2)_m$—, where m=2, 3, 4, 5 or 6, wherein the —$(CH_2)_m$— ring is unsubstituted or monosubstituted or polysubstituted by $C_{1-6}$-alkyl, aryl, O—$C_{1-6}$- alkyl and/or O—($C_{1-6}$-alkyl)-aryl or benzo-fused;

$R^3$ denotes H, $C_{1-12}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl, —($C_{1-6}$-alkyl)-heterocyclyl or C(=O)—$R^7$, $R^4$ denotes H, $C_{1-12}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl or —($C_{1-6}$-alkyl)-heterocyclyl, or $R^3$ and $R_4$ together form —$(CH_2)_n$—, where n=3, 4, 5, 6 or 7, or —$(CH_2)_2$—X—$(CH_2)_2$—, where X=O, S or $NR^8$, wherein —$(CH_2)_n$— or —$(CH_2)_2$—X—$(CH_2)_2$— is unsubstituted or substituted by $C_{1-6}$-alkyl;

$R^5$ and $R^6$ independently of one another denote $C_{1-12}$-alkyl, $C_{3-8}$-cycloalkyl, —($C_{1-6}$-alkyl)-$C_{3-8}$-cycloalkyl, aryl or ($C_{1-6}$-alkyl)-aryl, or together form —$(CH_2)_o$—, where o=3, 4, 5, 6 or 7, or —$(CH_2)_2$—Y—$(CH_2)_2$—, where Y=O, S or $NR^9$, wherein —$(CH_2)_o$— or —$(CH_2)_2$—Y—$(CH_2)_2$— is unsubstituted or substituted by $C_{1-6}$-alkyl;

A denotes aryl, heteroaryl, C(=O)$OR^{10}$ or 2-propyl; wherein $R^7$ denotes $C_{1-6}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl or —($C_{1-6}$-alkyl)-heterocyclyl;

$R^8$ and $R^9$ independently of one another denote H, $C_{1-6}$-alkyl, $C_{3-8}$-cycloalkyl, —($C_{1-6}$-alkyl)-$C_{3-8}$-cycloalkyl, aryl, —($C_{1-6}$-alkyl)-aryl or heterocyclyl;

$R^{10}$ denotes $C_{1-6}$-alkyl, $C_{3-8}$-cycloalkyl, —($C_{1-6}$-alkyl)-$C_{3-8}$-cycloalkyl, aryl or —($C_{1-6}$-alkyl)-aryl.

The compounds of the general structure (I) can be present as a racemate, or in the form of one or more of their diastereomers or one or more of their enantiomers.

DETAILED DESCRIPTION OF THE EMBODIMENTS

The following compounds of the general structure (I) are already known in the prior art (Synlett (1997), 177-178), without their use in a medicament or for the preparation of a medicament for treatment and/or prophylaxis of pain, urinary incontinence, itching, tinnitus aurium and/or diarrhoea being described: N,N-dimethyl-[phenyl-(2-pyrrolidin-1-yl-cyclohexyl)-methyl]-amine, N,N-dimethyl-[(2-morpholin-4-yl-cyclohexyl)-phenyl-methyl]-amine, 4-[phenyl-(2-pyrrolidin-1-yl-cyclohexyl)-methyl]-pyrrolidine, 4-[phenyl-(2-pyrrolidin-1-yl-cyclohexyl)-methyl]-morpholine, 1-[phenyl-(2-pyrrolidin-1-yl-cyclohexyl)-methyl]-piperidine, 1-[2-methyl-1-(2-pyrrolidin-1-yl-cyclohexyl)-propyl]-piperidine, N,N-dimethyl-(2-methyl-1,3-diphenyl-3-pyrrolidin-1-yl-propyl)-amine, N,N-dimethyl-(2-methyl-1,3-diphenyl-3-(N,N-diethylamino)-propyl)-amine, 4-(1,3-diphenyl-3-pyrrolidin-1-yl-propyl)-morpholine, N,N-dimethyl-(2-methyl-1-phenyl-3-(morpholin-4-yl)-pentyl)-amine, benzyl-[2-(dimethylamino-phenyl-methyl)-cyclohexyl]-amine and (2-methyl-1,3-diphenyl-3-piperidin-1-yl-propyl)-propyl-amine. The present invention therefore also provides these compounds inasmuch as processes according to the invention for their preparation, medicaments comprising them and their use for the preparation of medicaments for treatment and/or prophylaxis of pain, urinary incontinence, itching, tinnitus aurium and/or diarrhoea are concerned.

In the context of this invention, the terms "alkyl", "$C_{1-12}$-alkyl" and "$C_{1-6}$-alkyl" comprise acyclic saturated or unsaturated hydrocarbon radicals, which can be branched or straight-chain and unsubstituted or monosubstituted or polysubstituted by identical or different substituents, having (as in the case of $C_{1-12}$-alkyl) 1 to 12 (i.e. 1, 2, 3, 4, 5, 6, 7, 8, 9, 10, 11 or 12) or (as in the case of $C_{1-6}$-alkyl) 1 to 6 (i.e. 1, 2, 3, 4, 5 or 6) C atoms, i.e. $C_{1-12}$-alkanyls or $C_{1-6}$-alkanyls, $C_{2-12}$-alkenyls or $C_{2-6}$-alkenyls and $C_{2-12}$-alkynyls or $C_{2-6}$-alkynyls. "Alkenyls" here have at least one C—C double bond and "alkynyls" at least one C—C triple bond. Alkyl is advantageously chosen from the group which comprises methyl, ethyl, n-propyl, 2-propyl, n-butyl, iso-butyl, sec-butyl, tert-butyl, n-pentyl, iso-pentyl, neo-pentyl, n-hexyl, 2-hexyl, n-heptyl, n-octyl, n-nonyl, n-decyl, n-dodecyl; ethenyl (vinyl), ethynyl, propenyl (—CH$_2$CH═CH$_2$, —CH═CH—CH$_3$, —C(═CH$_2$)—CH$_3$), propynyl (—CH$_2$—C≡CH, —C≡C—CH$_3$), butenyl, butynyl, pentenyl, pentynyl, hexenyl, hexynyl, octenyl and octynyl.

In the context of this invention, "$C_{3-8}$-cycloalkyl" (or "cycloalkyl") denotes a cyclic saturated or unsaturated hydrocarbon radical having 3, 4, 5, 6, 7 or 8 C atoms, where the radical can be unsubstituted or monosubstituted or polysubstituted by identical or different substituents and optionally benzo-fused. By way of example, cycloalkyl represents cyclopropyl, cyclobutyl, cyclopentyl, cyclohexyl and cycloheptanyl.

For the purposes of the present invention, the term "aryl" is to be understood as a radical which is chosen from the group comprising phenyl, naphthyl, anthracenyl and biphenyl and is unsubstituted or monosubstituted or polysubstituted by identical or different substituents. Preferred substituents are $C_{1-6}$-alkyl, F, Cl, Br, I, CF$_3$, OR$^{11}$, OCF$_3$, SR$^{12}$, SO$_2$CH$_3$, SO$_2$CF$_3$, phenyl CN, CO$_2$R$^{13}$ and NO$_2$, wherein R$^{11}$, R$^{12}$ and R$^{13}$ independently of one another denote H, $C_{1-6}$-alkyl, $C_{3-8}$-cycloalkyl, phenyl, —($C_{1-6}$-alkyl)-$C_{3-8}$-cycloalkyl, benzyl or phenethyl. Aryl is preferably a phenyl, 1-naphthyl or 2-naphthyl which is unsubstituted or monosubstituted or polysubstituted by identical or different substituents, in particular an unsubstituted or monosubstituted phenyl.

The term "heterocyclyl" represents a monocyclic or polycyclic organic radical in which at least one ring contains 1 heteroatom or 2, 3, 4 or 5 identical or different heteroatoms which is/are chosen from the group containing N, O and S, where the radical is saturated or unsaturated and is unsubstituted or monosubstituted or polysubstituted by identical or different substituents. Examples of heterocyclyl radicals in the context of this invention are monocyclic five-, six- or seven-membered organic radicals with 1 heteroatom or 2, 3, 4 or 5 identical or different heteroatoms, which is/are nitrogen, oxygen and/or sulfur, and benzo-fused analogues thereof. A sub-group of heterocyclyl radicals is formed by the "heteroaryl" radicals, which are those heterocyclyls in which the ring, at least one of which is present, which contains the heteroatom/s is heteroaromatic. Each heteroaryl radical can be present as a radical which is unsubstituted or monosubstituted or polysubstituted by identical or different substituents. Examples of heterocyclyl radicals in the context of the present invention are pyrrolidinyl, tetrahydrofuryl, piperidinyl, piperazinyl and, in particular, morpholinyl. Examples of heteroaryl radicals are pyrrolyl, furanyl, thienyl, pyrazolyl, imidazolyl, pyridazinyl, pyrimidinyl, pyrazinyl and, in particular, pyridinyl, and benzo-fused analogues thereof. All these radicals can in each case be present as radicals which are unsubstituted or substituted.

For the purposes of the present invention, the terms "($C_{1-6}$-alkyl)-$C_{3-8}$-cycloalkyl", "($C_{1-6}$-alkyl)-heterocyclyl" and "($C_{1-6}$-alkyl)-aryl" mean that the cycloalkyl, heterocyclyl or aryl radical is bonded via a $C_{1-6}$-alkyl group to the compound substituted by it.

In connection with "alkyl", "alkanyl", "alkenyl", "alkynyl" and "cycloalkyl", the term "substituted" in the context of this invention is understood as meaning replacement of a hydrogen atom by, for example, F, Cl, Br, I, —CN, NH$_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, NO$_2$, SH, S-alkyl, S-aryl, S-alkyl-aryl, S-heterocyclyl, S-alkyl-OH, S-alkyl-SH, OH, O-alkyl, O-aryl, O-alkyl-aryl, O-heterocyclyl, O-alkyl-OH, CHO, C(═O)C$_{1-6}$-alkyl, C(═S)C$_{1-6}$-alkyl, C(═O)aryl, C(═S) aryl, C(═O)C$_{1-6}$-alkyl-aryl, C(═S)C$_{1-6}$-alkyl-aryl, C(═O)-heterocyclyl, C(═S)-heterocyclyl, CO$_2$H, CO$_2$-alkyl, CO$_2$-alkyl-aryl, C(═O)NH$_2$, C(═O)NH-alkyl, C(═O)NHaryl, C(═O)NH-heterocyclyl, C(═O)N(alkyl)$_2$, C(═O)N(alkyl-aryl)$_2$, C(═O)N(heterocyclyl)$_2$, SO-alkyl, SO$_2$-alkyl, SO$_2$-alkyl-aryl, SO$_2$NH$_2$, SO$_3$H, SO$_3$-alkyl, cycloalkyl, aryl or heterocyclyl, where polysubstituted radicals are to be understood as meaning those radicals which are polysubstituted, e.g. di- or trisubstituted, either on different or on the same atoms, for example, trisubstituted on the same C atom, such as in the case of CF$_3$ or —CH$_2$CF$_3$, or at different points, such as in the case of —CH(OH)—CH═CCl—CH$_2$Cl. Polysubstitution can be by identical or different substituents. CF$_3$ is particularly preferred as substituted alkyl for the purposes of the present invention.

In the context of this invention, in respect of "aryl", "heterocyclyl" and "heteroaryl", "monosubstituted" or "polysubstituted" is understood as meaning one or more, e.g. two, three or four, replacements of one or more hydrogen atoms of the ring system by a suitable substituent. Where the meaning of these suitable substituents is not defined elsewhere in the description or in the claims in connection with "aryl", "heterocyclyl" or "heteroaryl", suitable substituents are F, Cl, Br, I, CN, NH$_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, NO$_2$, SH, S-alkyl, S-cycloalkyl, S-aryl, S-alkyl-aryl, S-heterocyclyl, S-alkyl-OH, S-alkyl-SH, OH, O-alkyl, O-cycloalkyl, O-aryl, O-alkyl-aryl, O-heterocyclyl, O-alkyl-OH, CHO, C(═O)C$_{1-6}$-alkyl, C(═S)C$_{1-6}$-alkyl, C(═O) aryl, C(═S)aryl, C(═O)—C$_{1-6}$-alkyl-aryl, C(═S)C$_{1-6}$-alkyl-aryl, C(═O)-heterocyclyl, C(═S)-heterocyclyl, CO$_2$H, CO$_2$-alkyl, CO$_2$-alkyl-aryl, C(═O)NH$_2$, C(═O) NH-alkyl, C(═O)NHaryl, C(═O)NH-heterocyclyl, C(═O)N(alkyl)$_2$, C(═O)N(alkyl-aryl)$_2$, C(═O)N(heterocyclyl)$_2$, S(O)-alkyl, S(O)-aryl, SO$_2$-alkyl, SO$_2$-aryl, SO$_2$NH$_2$, SO$_3$H, CF$_3$, ═O, ═S; alkyl, cycloalkyl, aryl and/or heterocyclyl; on one or optionally various atoms (where a substituent can optionally be substituted in its turn). Polysubstitution here is by identical or different substituents. Particularly preferred substituents for aryl and heterocyclyl are $C_{1-6}$-alkyl, F, Cl, Br, I, CF$_3$, OR$^{11}$, OCF$_3$, SR$^{12}$, SO$_2$CH$_3$, SO$_2$CF$_3$, phenyl, CN, CO$_2$R$^{13}$ and/or NO$_2$, wherein R$^{11}$, R$^{12}$ and R$^{13}$ independently of one another denote H, $C_{1-6}$-alkyl, $C_{3-8}$-cycloalkyl, phenyl, —($C_{1-6}$-alkyl)-$C_{3-8}$-cycloalkyl, benzyl or phenethyl.

For the purposes of the present invention, "benzo-fused" means that a benzene ring is fused on to another ring.

Pharmaceutically acceptable salts in the context of this invention are those salts of compounds according to the general structure (I) according to the invention which are physiologically tolerated in pharmaceutical use—in particular when used on mammals and/or humans. Such pharmaceutically acceptable salts can be formed, for example, with inorganic or organic acids.

The pharmaceutically acceptable salts of compounds according to the invention are preferably formed with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed are, inter alia, hydrochlorides, hydrobromides, phosphates, carbonates, bicarbonates, formates, acetates, oxalates, succinates, tartrates, fumarates, citrates and glutamates. Solvates are also preferred, and in particular the hydrates of the compounds according to the invention, which can be obtained e.g. by crystallization from aqueous solution.

Preferred compounds of the general formula (I) or pharmaceutically acceptable salts thereof are those wherein $R^1$ denotes $C_{1-6}$-alkyl or aryl, $R^2$ denotes $C_{1-6}$-alkyl, aryl, —($C_{1-6}$-alkyl)-aryl or heteroaryl, wherein $R^1$ and $R^2$ are not at the same time aryl or aryl and heteroaryl, or $R^1$ and $R^2$ together form —$(CH_2)_m$—, where m=3, 4 or 5;

$R^3$ denotes H, $C_{1-6}$-alkyl, aryl, —($C_{1-6}$-alkyl)-aryl, heteroaryl or C(=O)—$R^7$, $R^4$ denotes H, $C_{1-6}$-alkyl, aryl, —($C_{1-6}$-alkyl)-aryl or heteroaryl, or $R^3$ and $R^4$ together form —$(CH_2)_n$—, where n=4, 5 or 6, or —$(CH_2)_2$—X—$(CH_2)_2$—, where X=O or $NR^8$;

$R^5$ and $R^6$ independently of one another denote $C_{1-6}$-alkyl, aryl or ($C_{1-6}$-alkyl)-aryl or together form —$(CH_2)_o$—, where o=4, 5 or 6, or —$(CH_2)_2$—Y—$(CH_2)_2$—, where Y=O or $NR^9$;

A denotes aryl, heteroaryl, C(=O)$OR^{10}$ or 2-propyl; wherein $R^7$ denotes $C_{1-6}$-alkyl, aryl, —($C_{1-6}$-alkyl)-aryl, heteroaryl or —($C_{1-6}$-alkyl)-heteroaryl;

$R^8$ and $R^9$ independently of one another denote H, $C_{1-6}$-alkyl, aryl, —($C_{1-6}$-alkyl)-aryl or heteroaryl;

$R^{10}$ denotes $C_{1-6}$-alkyl, aryl or —($C_{1-6}$-alkyl)-aryl;

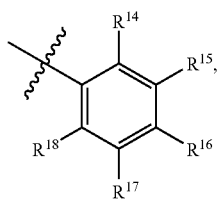

aryl is a radical which is chosen from the group which comprises

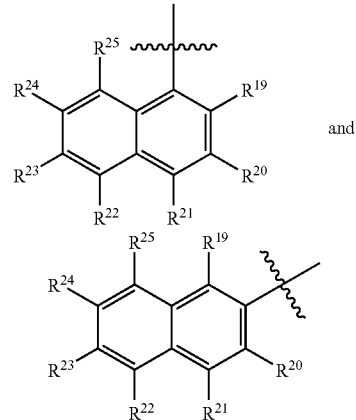

and $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ independently of one another denote H, $C_{1-6}$-alkyl, F, Cl, Br, I, $CF_3$, $OR^{11}$, $OCF_3$, $SR^{12}$, $SO_2CH_3$, $SO_2CF_3$, phenyl, CN, $CO_2R^{13}$ or $NO_2$; and $R^{11}$, $R^{12}$ and $R^{13}$ independently of one another denote H, $C_{1-6}$-alkyl, phenyl, benzyl or phenethyl.

Among these, particularly preferred compounds are those in which $R^1$ denotes methyl, ethyl, n-propyl, 2-propyl, n-butyl, iso-butyl, sec-butyl, tert-butyl or phenyl, $R^2$ denotes methyl, ethyl, n-propyl, 2-propyl, n-butyl, iso-butyl, sec-butyl, tert-butyl, phenyl, benzyl, phenethyl or pyridinyl, wherein $R^1$ and $R^2$ are not at the same time phenyl or phenyl and pyridinyl, or $R^1$ and $R^2$ together form —$(CH_2)_m$—, where m=3 or 4;

$R^3$ denotes H, methyl, ethyl, n-propyl, 2-propyl, n-butyl, iso-butyl, sec-butyl, tert-butyl, phenyl, —$CH_2$-$aryl^1$ or C(=O)—$R^7$, $R^4$ denotes H, methyl, ethyl, n-propyl, 2-propyl, n-butyl, iso-butyl, sec-butyl, tert-butyl, phenyl or —$CH_2$-$aryl^3$, or $R^3$ and $R^4$ together form —$(CH_2)_n$—, where n=4 or 5, or —$(CH_2)_2$—X—$(CH_2)_2$—, where X=O or $NR^8$;

$R^5$ and $R^6$ independently of one another denote methyl, ethyl, n-propyl, 2-propyl or —$CH_2$-phenyl, or together form —$(CH_2)_o$—, where o=4 or 5, or —$(CH_2)_2$—Y—$(CH_2)_2$—, where Y=O or $NR^9$;

A denotes $aryl^4$, pyridinyl which is unsubstituted or monosubstituted or polysubstituted by identical or different substituents, C(=O)$OR^{10}$ or 2-propyl; wherein $R^7$ denotes methyl, ethyl, n-propyl, 2-propyl, n-butyl, iso-butyl, sec-butyl, tert-butyl or $aryl^2$;

$R^8$ and $R^9$ independently of one another denote H, methyl or phenyl;

$R^{10}$ denotes methyl, ethyl, n-propyl, 2-propyl, n-butyl, tert-butyl or benzyl; and $aryl^1$, $aryl^2$, $aryl^3$ and $aryl^4$ independently of one another denote

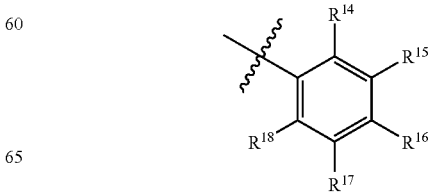

wherein 2, 3, 4 or 5 of the radicals $R^{14}$, $R^{15}$, $R^{16}$, $R^{17}$ and $R^{18}$ represent H and the other radicals of $R^{14}$, $R^{15}$, $R^{16}$, $R^{17}$ and $R^{18}$ independently of one another denote $C_{1-6}$-alkyl, F, Cl, Br, I, $CF_3$, $OR^{11}$, $OCF_3$, $SR^{12}$, $SO_2CH_3$, $SO_2CF_3$, phenyl, CN, $CO_2R^{13}$ or $NO_2$; and $R^{11}$, $R^{12}$ and $R^{13}$ independently of one another denote H, $C_{1-6}$-alkyl, phenyl, benzyl or phenethyl.

Very particularly preferred compounds of the general structure (I) according to the invention are those in which $R^1$ denotes methyl or ethyl, $R^2$ denotes methyl, ethyl or phenyl, or $R^1$ and $R^2$ together form —$(CH_2)_4$—;

$R^3$ denotes H, n-propyl, —$CH_2$-phenyl or C(=O)—$R^7$;

$R^4$ denotes H;

$R^5$ and $R^6$ each denote methyl or together form —$(CH_2)_2$—O—$(CH_2)_2$—;

A denotes phenyl, 2-chlorophenyl, 2-methoxyphenyl, 2-nitrophenyl or pyridin-3-yl; and $R^7$ denotes methyl, phenyl, 2-fluorophenyl, 2-chlorophenyl or 2-methylphenyl.

The compounds of the general structure (I) according to the invention always have at least three centres of asymmetry which are identified with * in the formula below:

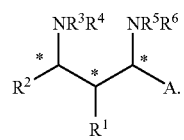

I

The compounds of the general structure (I) according to the invention can thus be present as a racemate, in the form of one or more of their diastereomers, i.e. in the diastereomerically pure form or as a mixture of two or more diastereomers, or in the form of one or more of their enantiomers, i.e. in the enantiomerically pure form or as a non-racemic mixture of enantiomers, and in particular both as the substance or as pharmaceutically acceptable salts of these compounds. The mixtures can be present in any desired mixing ratio of the stereoisomers.

It is preferable here that the compounds of the general formula (I) according to the invention, or one of their pharmaceutically acceptable salts, are present as diastereomers of the formula (syn,anti-I)

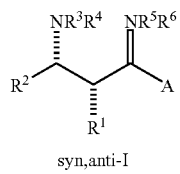

syn,anti-I and optionally in the enantiomerically pure form. The designation "syn,anti" chosen for identification of the relative configuration (relative stereochemistry) is to be understood as meaning that the two adjacent substituents $NR^3R^4$ and $R^1$ in the conformation drawn above point into the same spatial half (="syn"), while the two adjacent substituents $R^1$ and $NR^5R^6$ in the conformation drawn point into opposite spatial halves (="anti") (S. Masamune et al., J. Am. Chem. Soc. (1982) 104, 5521-5523).

Compounds of the general structure (I) or their pharmaceutically acceptable salts which are present as diastereomers of the formula (anti,anti-I)

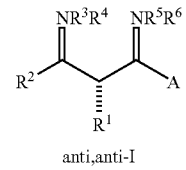

anti,anti-I and optionally in the enantiomerically pure form are also preferred. The designation "anti,anti" chosen for identification of the relative stereochemistry is to be understood as meaning that the two adjacent substituents $NR^3R^4$ and $R^1$ in the conformation drawn point into opposite spatial halves (="anti") just as the two adjacent substituents $R^1$ and $NR^5R^6$ do.

Compounds of the general structure (I) or their pharmaceutically acceptable salts which are present as diastereomers of the formula (anti,syn-I)

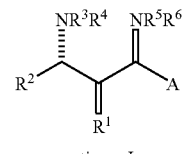

anti,syn-I and optionally in the enantiomerically pure form are furthermore preferred. The designation "anti,syn" chosen for identification of the relative stereochemistry is to be understood as meaning that the two adjacent substituents $NR^3R^4$ and $R^1$ in the conformation drawn point into opposite spatial halves (="anti"), while the two adjacent substituents $R^1$ and $NR^5R^6$ in the conformation drawn point into the same spatial half (="syn").

Compounds of the general structure (I) or their pharmaceutically acceptable salts which are furthermore preferred are those which are present as diastereomers of the formula (syn,syn-I)

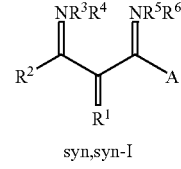

syn,syn-I and optionally in the enantiomerically pure form. The designation "syn,syn" chosen for identification of the relative stereochemistry is to be understood as meaning that the two adjacent substituents $NR^3R^4$ and $R^1$ in the conformation drawn point into the same spatial half (="syn") just as the two adjacent substituents $R^1$ and $NR^5R^6$ do.

Compounds by way of example and advantageous compounds of the present invention are chosen from the group which comprises (syn,syn)-N-[2-(dimethylaminopyridin-3-ylmethyl)cyclohexyl]-benzamide or its hydrochloride
(syn,syn)-2-(dimethylaminopyridin-3-ylmethyl)cyclohexylamine or its hydrochloride
(syn,syn)-N-[2-(dimethylaminopyridin-3-ylmethyl)cyclohexyl]-2-fluorobenzamide or its hydrochloride
(syn,syn)-2-chloro-N-[2-(dimethylaminopyridin-3-ylmethyl)cyclohexyl]-benzamide or its hydrochloride
(anti,anti)-N-[2-(dimethylaminopyridin-3-ylmethyl)cyclohexyl]-benzamide or its hydrochloride
(anti,anti)-2-(dimethylaminopyridin-3-ylmethyl)cyclohexylamine or its hydrochloride
(anti,anti)-N-[2-(dimethylaminopyridin-3-ylmethyl)cyclohexyl]-2-fluorobenzamide or its hydrochloride
(anti,anti)-2-chloro-N-[2-(dimethylaminopyridin-3-ylmethyl)cyclohexyl]benzamide or its hydrochloride
(anti,anti)-N-[2-(dimethylaminopyridin-3-ylmethyl)cyclohexyl]-2-methylbenzamide or its hydrochloride
(syn,syn)-N-[2-(dimethylaminopyridin-3-ylmethyl)cyclohexyl]-2-methylbenzamide or its hydrochloride
(syn,syn)-N-[2-(dimethylaminopyridin-3-ylmethyl)cyclohexyl]acetamide or its hydrochloride
(anti,anti)-N-[2-(dimethylaminopyridin-3-ylmethyl)cyclohexyl]acetamide or its hydrochloride
(syn,syn)-N-[2-(dimethylaminophenylmethyl)cyclohexyl]-2-fluorobenzamide or its hydrochloride
(syn,syn)-2-(dimethylaminophenylmethyl)cyclohexylamine or its hydrochloride
(syn,syn)-N-[2-(dimethylamino-phenyl-methyl)-cyclohexyl]-acetamide or its hydrochloride
(syn,syn)-N-[2-(dimethylamino-phenyl-methyl)-cyclohexyl]-benzamide or its hydrochloride
(syn,syn)-2-chloro-N-[2-(dimethylamino-phenyl-methyl)-cyclohexyl]-benzamide or its hydrochloride
(syn,syn)-N-[2-(dimethylamino-phenyl-methyl)-cyclohexyl]-2-methyl-benzamide or its hydrochloride
(anti,anti)-N-[2-(dimethylamino-phenyl-methyl)-cyclohexyl]-acetamide or its hydrochloride
(anti,anti)-2-(dimethylamino-phenyl-methyl)-cyclohexylamine or its hydrochloride
(anti,anti)-N-[2-(dimethylamino-phenyl-methyl)-cyclohexyl]-benzamide or its hydrochloride
(anti,anti)-N-[2-(dimethylamino-phenyl-methyl)-cyclohexyl]-2-methyl-benzamide or its hydrochloride
(syn,syn)-2-chloro-N-{2-[(2-chloro-phenyl)-dimethylamino-methyl]-cyclohexyl}-benzamide or its hydrochloride
(syn,syn)-2-[(2-chloro-phenyl)-dimethylamino-methyl]-cyclohexylamine or its hydrochloride
(anti,anti)-2-chloro-N-{2-[(2-chloro-phenyl)-dimethylamino-methyl]-cyclohexyl}-benzamide or its hydrochloride
(anti,anti)-2-[(2-chloro-phenyl)-dimethylamino-methyl]-cyclohexylamine or its hydrochloride
(syn,syn)-N-{2-[(2-chloro-phenyl)-dimethylamino-methyl]-cyclohexyl}-2-fluoro-benzamide or its hydrochloride
(anti,anti)-N-{2-[dimethylamino-(2-nitro-phenyl)-methyl]-cyclohexyl}-benzamide or its hydrochloride
(anti,anti)-2-[dimethylamino-(2-nitro-phenyl)-methyl]-cyclohexylamine or its hydrochloride
(anti,anti)-N-{2-[dimethylamino-(2-nitro-phenyl)-methyl]-cyclohexyl}-2-fluoro-benzamide or its hydrochloride
(anti,anti)-2-chloro-N-{2-[dimethylamino-(2-nitro-phenyl)-methyl]-cyclohexyl}-benzamide or its hydrochloride
(anti,anti)-N-{2-[dimethylamino-(2-nitro-phenyl)-methyl]-cyclohexyl}-2-methyl-benzamide or its hydrochloride
(syn,syn)-N-{2-[dimethylamino-(2-nitro-phenyl)-methyl]-cyclohexyl}-acetamide or its hydrochloride
(syn,syn)-N-2-[dimethylamino-(2-nitro-phenyl)-methyl]-cyclohexylamine or its hydrochloride
(anti,anti)-N-{2-[(2-chloro-phenyl)-dimethylamino-methyl]-cyclohexyl}-acetamide or its hydrochloride
(syn,anti)-2-(dimethylamino-phenyl-methyl)-cyclohexylamine
(syn,anti)-N-[2-(dimethylamino-phenyl-methyl)-cyclohexyl]-benzamide
(anti,anti)-N-{2-[dimethylamino-(2-methoxy-phenyl)-methyl]-cyclohexyl}-benzamide
(anti,anti)-N-{2-[dimethylamino-(2-nitro-phenyl)-methyl]-cyclohexyl}-benzamide
(anti,anti)-N-{2-[(2-chloro-phenyl)-dimethylamino-methyl]-cyclohexyl}-benzamide
(anti,anti)-N-{2-[dimethylamino-(2-methoxy-phenyl)-methyl]-cyclohexyl}-acetamide
(anti,anti)-2-[dimethylamino-(2-methoxy-phenyl)-methyl]-cyclohexylamine
(anti,anti)-N-{2-[(2-chloro-phenyl)-dimethylamino-methyl]-cyclohexyl}-acetamide
(anti,anti)-N-{2-[dimethylamino-(2-nitro-phenyl)-methyl]-cyclohexyl}-acetamide
(anti,anti)-2-[dimethylamino-(2-nitro-phenyl)-methyl]-cyclohexylamine
(syn,syn)-2-(dimethylamino-phenyl-methyl)-cyclohexylamine
(syn,syn)-2-[(2-chloro-phenyl)-dimethylamino-methyl]-cyclohexylamine
(anti,anti)-2-chloro-N-(3-dimethylamino-1-ethyl-2-methyl-3-phenyl-propyl)-benzamide
(anti,anti)-3-dimethylamino-1-ethyl-2-methyl-3-phenyl-propylamine
(syn,anti)-2-(dimethylamino-phenyl-methyl)-cyclohexyl-N-(n-propyl)amine
(syn,anti)-2-(morpholin-4-yl-phenyl-methyl)-cyclohexyl-N-(n-propyl)-amine
(syn,anti)-2,N,N-trimethyl-1,3-diphenyl-N'-propyl-propane-1,3-diamine
(syn,anti)-2-(dimethylamino-phenyl-methyl)-cyclohexyl-N-benzylamine
(syn,anti)-2-(morpholin-4-yl-phenyl-methyl)-cyclohexyl-N-benzylamine
(syn,anti)-2,N,N-trimethyl-1,3-diphenyl-N'-benzyl-propane-1,3-diamine
(syn,anti)-2-(dimethylamino-phenyl-methyl)-cyclohexylamine
(syn,anti)-2-(morpholin-4-yl-phenyl-methyl)-cyclohexylamine
(syn,anti)-2,N,N-trimethyl-1,3-diphenyl-propane-1,3-diamine
(syn,anti)-2-[(2-chlorophenyl)-dimethylamino-methyl]-cyclohexylamine
(anti,anti)-2-[(2-chlorophenyl)-dimethylamino-methyl]-cyclohexylamine
(syn,syn)-2-(dimethylamino-phenyl-methyl)-cyclohexylamine
(anti,anti)-2-(dimethylamino-phenyl-methyl)-cyclohexylamine
(syn,syn)-2-[(2-chlorophenyl)-dimethylamino-methyl]-cyclohexylamine
(syn,syn)-2-(dimethylamino-pyridin-3-yl-methyl)-cyclohexylamine (anti,anti)-2-(dimethylamino-pyridin-3-yl-methyl)-cyclohexylamine (syn,syn)-2-(dimethylamino-(2-methoxyphenyl)-methyl)-cyclohexylamine (anti,anti)-2-(dimethylamino-(2-methoxyphenyl)-methyl)-cyclohexylamine (syn,syn)-2-(dimethylamino-(2-nitrophenyl)-methyl)-cyclohexylamine (anti,anti)-2-(dimethylamino-(2-nitrophenyl)-methyl)-cyclohexylamine.

The present invention also provides processes for the preparation of the compounds of the general structure (I). Thus, compounds of the general structure (I) in which $R^3$ represents H, $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl or —($C_{1-6}$-alkyl)-heterocyclyl and $R^4$ represents hydrogen can be obtained by reduction of the corresponding imine of the general formula (II)

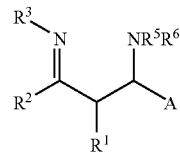

II

Suitable reducing agents are, for example, complex hydrides, such as e.g. $ZnCNBH_3$, which can be formed in situ by reaction of sodium cyanoborohydride with anhydrous zinc(II) chloride in an anhydrous organic solvent, diisobutylaluminium hydride (=DIBAH, DIBAL), L-Selectride (i.e. lithium tri-sec-butylborohydride) and $LiBH_4$, $NaBH_4$, $NaBH_3CN$ and $NaBH(OC(=O)CH_3)_3$. The reduction is carried out here at temperatures from $-70°$ C. to $+65°$ C., preferably $0°$ C. to $40°$ C., over a period of 0.5 h to 24 h. This imine reduction process in general gives the diamine (I) as a mixture of various conceivable stereoisomers (diastereomer mixture). Alternatively, the reduction can also be carried out with hydrogen (under an $H_2$ partial pressure of 1 to 50 bar) in the presence of a suitable transition metal catalyst, e.g. Ni, Pd, Pt or $PtO_2$, preferably in situ.

Surprisingly, it has been found that the imine reduction process described above can also be adapted to diastereoselective synthesis of (anti,anti-I) or (syn,syn-I) (where $R^3$ and $R^4$=H): If an imine (II) with the relative configuration anti

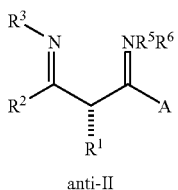

anti-II is reacted with a suitable reducing agent, in particular zinc cyanoborohydride, $LiBH_4$, $NaBH_4$, $NaBH_3CN$ or $NaBH(OC(=O)CH_3)_3$, in an alcoholic solvent, the diamine (I) with the relative configuration anti,anti

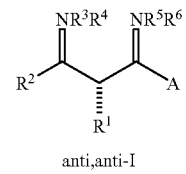

anti,anti-I is obtained with a high stereoselectivity. The reduction is preferably carried out in methanol with slow warming from $0°$ C. to room temperature over 8 to 24 h, in particular 10 to 14 h.

On the other hand, if the imine (anti-II) is reacted with a suitable reducing agent in an ethereal solvent, the diamine (I) with the relative configuration syn,syn is obtained virtually exclusively:

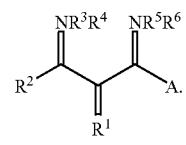

syn,syn-I

This reduction is preferably carried out with L-Selectride or diisobutylaluminium hydride (DIBAH), in particular in THF and with warming from $0°$ C. to room temperature over 8 to 24 h, in particular 10 to 14 h.

To obtain the diastereomers of the diamine (I) with the relative configuration syn,anti or anti,syn, the diastereomer product mixture of the imine reduction process which has not been carried out stereoselectively can be subjected, for example, to a fractional crystallization, also of its salts, or a chromatographic separation.

The imines of the formula (II) employed in the non-stereoselective imine reduction process according to the invention are readily accessible from the corresponding Mannich bases of the general structure (III)

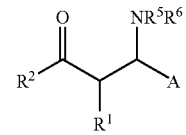

III wherein $R^1$, $R^2$, $R^5$, $R^6$ and A are as defined for formula (I) and (II), by reaction with ammonia or an equivalent reagent (if $R^3$ in formula (II) denotes H) or with a primary amine $R^3NH_2$ (if $R^3$ in (II) denotes not H but $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl or —($C_{1-6}$-alkyl)-heterocyclyl. In the case where $R^3$=H, it is preferable to react the Mannich base (III) with ammonium acetate in an ethereal or alcoholic solvent to give the imine (II), which in its turn is reduced, preferably in situ, to the compound (I) according to the invention. The reaction of (III) with ammonium acetate can thus be carried out in anhydrous tetrahydrofuran (THF) at temperatures of $0°$ C. to $80°$ C., preferably at 20 to $25°$ C., and with a reaction time of 0.5 h to 12 h, preferably 30 min to 120 min, in particular 60 min, in particular if the subsequent reduction is carried out in THF. Alternatively, the reaction of (III) with ammonium acetate can also be carried out in anhydrous methanol at temperatures of 0° C. to 80° C., preferably at 20 to 25° C., and with a reaction time of 0.5 h to 12 h, preferably 30 min to 120 min, in particular 60 min, in particular if the subsequent reduction is carried out in methanol.

The anti-configured imines (anti-II) are accessible analogously starting from the corresponding anti-configured Mannich bases (anti-III)

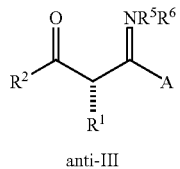

anti-III by reacting these with the primary amine $R^3NH_2$ or with ammonia or an equivalent reagent, such as e.g. ammonium acetate, under the conditions described above for the formation of (II).

The preparation of the Mannich bases (III) is known per se from the literature and is described in detail e.g. in the patent applications EP 1 043 307 A2 and EP 1 043 306 A2, which are herewith incorporated into the disclosure of the present invention. The 1,4-addition of secondary amines $HNR^5R^6$ on to enones of the general structure (XI)—which in their turn are obtained by aldol condensation of ketones of the formula (IX) with aldehydes of the general formula (X)—thus leads to the desired Mannich bases (II) (U.S. Pat. No. 4,017,637), which as a rule are obtained as a mixture of the stereoisomers.

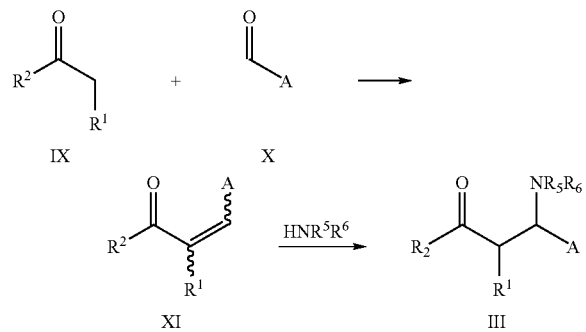

The meaning of the radicals $R^1$, $R^2$, $R^5$, $R^6$ and A corresponds to the meaning for the formulae (I) and (II).

The Mannich bases (III) obtained in this way can be used as a mixture of stereoisomers or can be separated into their diastereomers employing processes well-known in the prior art, such as e.g. crystallization or chromatography, and reacted as such.

Alternatively, Mannich bases with preferably the anti-configuration can be prepared diastereoselectively by reaction of enamines of the general structure (XII), wherein the radicals R e.g. denote alkyl or together form —$(CH_2)_4$— or —$(CH_2)_5$—, with iminium salts of the general structure (VIII), in which Z— is a suitable counter-ion, such as e.g. Cl—, Br—, I— or $AlCl_4^-$ (EP 1 043 307 A2 and EP 1 043 306 A2).

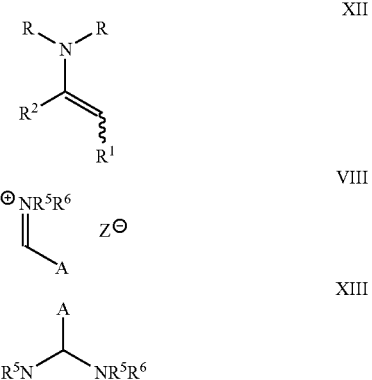

The enamines are prepared by processes known from the literature from ketones of the general structure (IX) and secondary amines, e.g. dimethylamine, pyrrolidine, piperidine or morpholine (Acta Chem. Scand. B 38 (1984) 49-53). The iminium salts (VIII) are prepared by processes known from the literature, e.g. by reaction of aminals of the general structure (XIII) with acid chlorides, e.g. acetyl chloride or thionyl chloride (Houben-Weyl—Methoden der Organischen Chemie, E21b (1995) 1925-1929) or by reaction of aldehydes of the formula (X) with secondary amines in the presence of sodium iodide, trimethylsilyl iodide and triethylamine (Synlett (1997) 974-976). The iminium salts (VIII) do not have to be isolated here, but can also be produced in situ and reacted with the enamines of the formula (XII), preferably to give the anti-Mannich bases (anti-III) (Angew. Chem. 106 (1994) 2531-2533). It is also possible to react ketones of the general structure (IX) directly with iminium salts (VIII) to give Mannich bases (III). In this case also, the Mannich bases (anti-III) with the anti-configuration are preferably formed.

From the anti-configured Mannich bases (anti-III), the corresponding syn-configured isomers (syn-III) can also be obtained, if necessary, by dissolving the Mannich base (anti-III) in a suitable solvent, e.g. an alcohol, such as methanol or ethanol, or water, adding a sufficiently strong acid, e.g. aqueous hydrochloric acid, dilute sulfuric acid or conc. acetic acid, and stirring the mixture for about 8 to 24 h; for the desired epimerization, it is essential here that the dissolved Mannich base (III) does not precipitate out or crystallize out of the solution, but remains in solution. After removal of the solvent, the anti-Mannich base (anti-III) and the syn-Mannich base (syn-III) are obtained as a diastereomer mixture, usually in a ratio of 1:1, which can be separated by conventional methods (crystallization, chromatography).

Another process according to the invention for the preparation of the compounds of the general structure (I) according to the invention in which $R^3$ and $R^4$ each denote H starts from an amino-alcohol of the general structure (IV), which is converted in a process step (a) into the corresponding mesylate or tosylate of the formula (V), wherein L denotes mesyl ($CH_3SO_2$—) or tosyl (4-$CH_3$-phenyl-$SO_2$—), for example by reaction of (IV) with mesyl chloride ($CH_3SO_2Cl$) or tosyl chloride (p-toluensulfonic acid chloride, 4-$CH_3$-phenyl-$SO_2Cl$) in the presence of a base (e.g. triethylamine); the mesylate or tosylate (V) is then reacted in a process step (b), for example, with sodium azide to give the azide (VI), which is converted in a process step (c), with reduction, into the diamine of the formula (I) according to the invention. The reduction is carried out here by processes known from the literature, e.g. with sodium borohydride in the presence of catalytic amounts of cobalt(II) bromide (D. M. Tschaen et al., J. Org. Chem. (1995) 60, 4324-4330) or with lithium aluminium hydride in diethyl ether.

This process can also be applied such that a compound of the formula (I) according to the invention is preferably obtained in a particular relative configuration. If an amino-alcohol of the general structure (anti,anti-IV)—an amino-alcohol (I) with the relative configuration (anti,anti)—is used as the starting substance, process step (a') preferably proceeds with the relative stereochemistry being retained to give the compound (anti,anti-V), while the subsequent azide formation (b') proceeds with inversion of the configuration of the stereo-centre on the O-L carbon atom and thus results in the azide (syn,anti-VI). Subsequent reduction of (syn,anti-VI) results in the diamine (syn,anti-I)

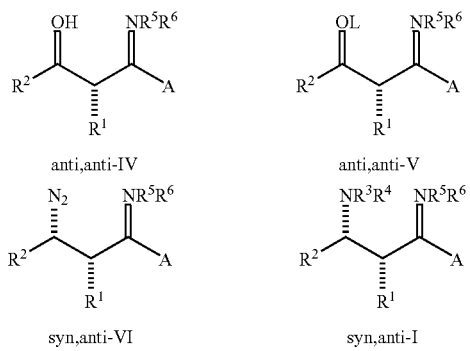

anti,anti-IV anti,anti-V
syn,anti-VI syn,anti-I

The diamine (anti,anti-I) is correspondingly also accessible stereoselectively if the process according to the invention starts with an amino-alcohol of the general structure (syn,anti-IV) and leads via the mesylate or tosylate of the general structure (syn,anti-V) to the azide of the general structure (anti,anti-VI), which is finally reduced to the diamine (anti,anti-I).

The amino-alcohols of the formula (IV) employed in this process are obtained in accordance with EP 0 143 306 A2 starting from the corresponding Mannich bases (III) by reduction with a reducing agent, such as e.g. sodium borohydride, sodium cyanoborohydride, lithium aluminium hydride, diisobutylaluminium hydride or a complex analogue of these compounds, at −70 to +110° C. in suitable solvents, e.g. diethyl ether, THF, methanol or ethanol. For example, if a Mannich base with the anti-configuration (anti-III) is used as the starting substance, the corresponding (anti,anti-IV) amino-alcohol is obtained by reduction with NaBH$_4$ in ethanol at room temperature over a reaction time of 8 to 16 h. On the other hand, if DIBAH or L-Selectride in THF is used for reduction of the Mannich base (anti-III), the (syn,anti-IV)-amino alcohol is obtained in a high diastereomer purity. On reduction of a Mannich base (III) which is not present in a diastereomerically pure or concentrated form, a mixture of the various stereoisomers of the amino-alcohol (IV) is usually obtained, which—if necessary—can be separated into the diastereomers and optionally also the enantiomers by known methods (crystallization, chromatography).

Alternatively to the tosyl/mesyl-azide process, the amino-alcohol (IV) can also be converted into the corresponding diamine (I) by means of the Mitsunobu reaction by reaction first with azodicarboxylic acid dimethyl or diethyl ester, triphenylphosphane and a phthalimide and then with hydrazine (O. Mitsunobu, Synthesis (1981) 1-28). Since this reaction proceeds with inversion of the stereochemistry on the O carbon atom, with its aid the diamine (syn,anti-I) can be obtained stereoselectively from the alcohol (anti,anti-IV), while the diamine (anti,anti-I) can be obtained stereoselectively from (syn,anti-IV).

In another process according to the invention, compounds of the general structure (I) where $R^3$=H, $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl or —($C_{1-6}$-alkyl)-heterocyclyl and $R^4$=H—and in particular preferably the diastereomers (syn,anti-I) (with the relative configuration syn,anti)—are obtained, the process being characterized by the following process steps:

(aa) Reaction of an imine of the general structure (VII)

VII wherein $R^1$ and $R^2$ are as defined for formula (I) and $R^3$ denotes H, $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl or —($C_{1-6}$-alkyl)-heterocyclyl, with an iminium salt of the general structure (VIII)

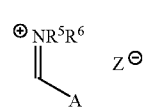

VIII wherein $R^5$, $R^6$, A and Z—are as defined above; and (bb) subsequent reduction of the intermediate product/s formed in process step (aa). The reduction is preferably carried out with a complex hydride or with molecular hydrogen ($H_2$ partial pressure of 1 to 50 bar) in the presence of a transition metal catalyst (Ni, Pd, Pt, PtO$_2$).

Suitable complex hydrides are e.g. sodium borohydride, sodium cyanoborohydride, lithium aluminium hydride, diisobutylaluminium hydride or a complex analogue of these compounds, which can be employed at −70 to +110° C. in suitable solvents, e.g. diethyl ether, THF, methanol or ethanol, optionally as a mixture with methylene chloride.

The imines (VII) are obtainable starting from the corresponding ketones (IX) by reaction with ammonia or ammonium acetate ($R^3$=H) or primary amines $R^3NH_2$ ($R^3\neq H$) by processes known from the literature (J. March, Advanced Organic Chemistry, New York, Chichester, Brisbane, Toronto, Singapore, 3rd ed., (1985), p. 796-798).

If an imine (VII) for which $R^3$ denotes —(CH$_2$)-phenyl, wherein phenyl can be substituted by $C_{1-6}$-alkyl, is used in this (imine+iminium salt) process, the imine (VII) is thus an N-benzyl-substituted imine (wherein the benzyl radical can be alkyl-substituted), this benzyl radical in the product (I)

according to the invention where $R^3$=benzyl (optionally alkyl-substituted) can be removed by reaction with hydrogen ($H_2$) in the presence of a transition metal (e.g. palladium, platinum or nickel) and the diamine (I) where $R^3$=$R^4$=H can thus be obtained. This process step (cc) is preferably carried out with 10% palladium on carbon as the transition metal, preferably in methanol.

Syn,anti-configured diamines of the general structure (I) are thus also accessible diastereoselectively with this process according to the invention.

Compounds of the general structure (I) where $R^3$=H and $R^4$=H, $C_{1-12}$-alkyl, $C_{3-8}$-cycloalkyl, aryl, —($C_{1-6}$-alkyl)-$C_{3-8}$- cycloalkyl, —($C_{1-6}$-alkyl)-aryl, heterocyclyl or —($C_{1-6}$-alkyl)-heterocyclyl can be converted—regardless of whether they are present as a racemate or in the form of one or more diastereomers or one or more enantiomers—by reaction with an acylating reagent into the corresponding compounds of the general structure (I) where $R^3$=C(=O)—$R^7$, wherein $R^7$ is as defined above. The acylating agent is preferably an acid chloride of the general formula $R^7$—C(=O)—Cl, wherein $R^7$ denotes $C_{1-6}$-alkyl, aryl, —($C_{1-6}$-alkyl)-aryl, heterocyclyl or —($C_{1-6}$-alkyl)-heterocyclyl.

In a manner known from the literature, the compounds of the general structure (I) where $R^3$=H and $R^4$=H, $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl or —($C_{1-6}$-alkyl)-heterocyclyl can also be alkylated or subjected to a reductive amination with aldehydes or ketones (see e.g. J. March, Advanced Organic Chemistry, New York, Chichester, Brisbane, Toronto, Singapore, 3rd ed., (1985), 798-800), so that the corresponding compounds (I) in which $R^3$ and/or $R^4$ denote/s $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl or —($C_{1-6}$-alkyl)-heterocyclyl are readily accessible. Diamines of the general structure (I) where $R_3$ (or $R^4$)=H can then likewise be subjected to an acylation (so that $R^3$ or $R^4$ respectively denotes —C(=O)—$R^7$), preferably with an acid chloride Cl—C(=O)—$R^7$ as defined above.

The compounds of the general formula (I) according to the invention in which the radicals $R^3$ and $R^4$ denote $C_{1-12}$-alkyl, —($C_{1-6}$-alkyl)-aryl, heterocyclyl or —($C_{1-6}$-alkyl)-heterocyclyl or together form —($CH_2$)$_n$—, where n=3, 4, 5, 6 or 7, or —($CH_2$)$_2$—X—($CH_2$)$_2$—, where X=O, S or $NR^8$, wherein —($CH_2$)$_n$— or —($CH_2$)$_2$—X—($CH_2$)$_2$— is unsubstituted or substituted by $C_{1-6}$-alkyl, are also accessible, for example, by reaction of the corresponding enamine (XII) with a corresponding iminium salt (VIII) and subsequent reduction with, for example, $NaBH_4$ in methanol (Synlett (1997) 177-178).

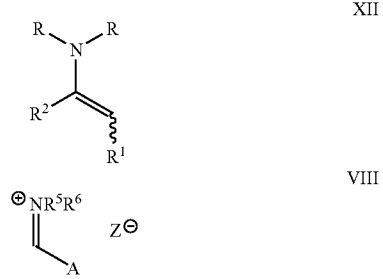

The syn,anti diastereomers of the compound (I) are preferably formed here.

The starting compounds, reagents and solvents employed in the processes used for the preparation of the diamines of the general structure (I) according to the invention are, unless stated otherwise in the description, commercially obtainable (from Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen; TCI, Japan) or can be prepared by processes generally known in the prior art.

The compounds of the general structure (I) according to the invention can be isolated either as the substance or as a salt. The compound of the general structure (I) according to the invention is usually obtained after the reaction has been carried out in accordance with the process according to the invention described above and subsequent conventional working up. The compound of the general structure (I) obtained in this way or formed in situ without isolation can then be converted, for example, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid, into the corresponding salt. The salts formed are, inter alia, hydrochlorides, hydrobromides, phosphates, carbonates, bicarbonates, formates, acetates, oxalates, succinates, tartrates, fumarates, citrates and glutamates. The particularly preferred hydrochloride formation can also be brought about by adding, advantageously in the presence of water, trimethylsilyl chloride (TMSCl) to the base, which is dissolved in a suitable organic solvent, such as e.g. butan-2-one (methyl ethyl ketone).

If the compounds of the general structure (I) are obtained in the preparation process according to the invention as racemates or as mixtures of their various enantiomers and/or diastereomers, these mixtures can be separated by processes well-known in the prior art. Suitable methods are, inter alia, chromatographic separation processes, in particular liquid chromatography processes under normal or increased pressure, preferably MPLC and HPLC processes, and processes of fractional crystallization. In these, in particular, individual enantiomers can be separated from one another e.g. by means of HPLC on a chiral phase or by means of crystallization of diastereomeric salts formed with chiral acids, for example (+)-tartaric acid, (−)-tartaric acid or (+)-10-camphorsulfonic acid.

The present invention also provides a medicament comprising at least one compound of the general structure (I) as defined above or one of its pharmaceutical salts, in particular the hydrochloride salt. The medicament according to the invention preferably comprises, in a pharmaceutical composition, at least one of the compounds mentioned above by way of example as the substance or as a pharmaceutically acceptable salt and optionally further active compounds and auxiliary substances. The diamine (I) according to the invention can be present here as a racemate or in the form of one or more diastereomers or one or more enantiomers.

Since the compounds of the general structure (I) according to the invention have surprisingly proved to have an analgesic action, the medicaments according to the invention comprising them are preferably employed in the prophylaxis and/or treatment of states of pain, such as e.g. acute pain, chronic pain or neuropathic pain, in particular severe to very severe pain. It has also been found that the medicaments according to the invention can be employed for treatment and/or prophylaxis of diarrhoea, urinary incontinence, itching and/or tinnitus aurium.

The present invention also provides the use of a diamine of the formula (I) or of one of its pharmaceutically acceptable salts for the preparation of a medicament for prophylaxis and/or treatment of pain, diarrhoea, urinary incontinence, itching and/or tinnitus aurium.

The medicaments, medical preparations and pharmaceutical compositions according to the invention can be present and administered as liquid, semi-solid or solid medicament forms and in the form of e.g. injection solutions, drops, juices, syrups, sprays, suspensions, granules, tablets, pellets, transdermal therapeutic systems, capsules, patches, suppositories, ointments, creams, lotions, gels, emulsions or aerosols, and in addition to at least one compound of the general structure (I) according to the invention, comprise, depending on the galenical form and depending on the administration route, pharmaceutical auxiliary substances, such as e.g. carrier materials, fillers, solvents, diluents, surface-active substances, dyestuffs, preservatives, disintegrating agents, slip agents, lubricants, aromas and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The choice of auxiliary substances and the amounts thereof to be employed depends on whether the medicament/medical preparation is to be administered orally, subcutaneously, parenterally, intravenously, vaginally, pulmonally, intraperitoneally, transdermally, intramuscularly, nasally, bucally, rectally or locally, for example on infections on the skin, the mucous membranes and the eyes. Formulations in the form of tablets, coated tablets, capsules, granules, drops, juices and syrups, inter alia, are suitable for oral administration, and solutions, suspensions, easily reconstitutable powders for inhalation and sprays are suitable for parenteral, topical and inhalatory administration. Compounds of the general structure (I) according to the invention in a depot in dissolved form or in a patch, optionally with the addition of agents which promote penetration through the skin, are suitable formulations for percutaneous administration. Formulation forms which can be used rectally, transmucosally, parenterally, orally or percutaneously can release the compounds of the general structure (I) according to the invention in a delayed manner.

The medicaments and pharmaceutical compositions according to the invention are prepared with the aid of agents, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus e.g. for a solid formulation, such as a tablet, the active compound of the medicament, i.e. a compound of the general structure (I) or one of its pharmaceutically acceptable salts, can be granulated with a pharmaceutical carrier, e.g. conventional tablet constituents, such as maize starch, lactose, sucrose, sorbitol, talc, magnesium stearate, dicalcium phosphate or pharmaceutically acceptable gums, and pharmaceutical diluents, such as e.g. water, in order to form a solid composition which comprises a compound according to the invention or a pharmaceutically acceptable salt thereof in homogeneous distribution. Homogeneous distribution is understood here as meaning that the active compound is distributed uniformly over the entire composition, so this can readily be divided into unit dose forms which have the same action, such as tablets, pills or capsules. The solid composition is then divided into unit dose forms. The tablets or pills of the medicament according to the invention or of the compositions according to the invention can also be coated or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

The amount of active compound to be administered to the patient varies and depends on the weight, the age and the case history of the patient, and on the mode of administration, the indication and the severity of the disease. 0.005 to 500 mg/kg, in particular 0.05 to 5 mg/kg, preferably 2 to 250 mg/kg of body weight of at least one compound of the general structure (I) according to the invention are usually administered.

The present invention is explained further in the following by examples, without limiting it thereto.

EXAMPLES

Introduction

The chemicals and solvents employed were purchased from Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen and TCI, Japan or synthesized by conventional processes known in the prior art.

Anhydrous THF was freshly distilled over potassium under an argon atmosphere.

Thin layer chromatography analyses were carried out with HPTLC pre-coated plates, silica gel 60 F 254 from E. Merck, Darmstadt. Silica gel 60 (0.040-0.063 mm) from E. Merck, Darmstadt, or $Al_2O_3$, neutral, from Macherey-Nagel, Düren was employed as the stationary phase for the column chromatography and MPLC.

The yields of the compounds prepared are not optimized. All the temperatures stated are uncorrected.

The mixing ratios of the mobile phases for chromatography analyses are always stated in volume/volume (V/V).

ESI mass spectra were recorded with an LCQ Classic Mass Spectrometer from Finnigan, and the $^1$H- and $^{13}$C-NMR spectra were recorded with a 300-(75-)MHz-Avance-DPX-300-NMR apparatus, a 600-(150-)MHz-Avance-DRX-600 NMR apparatus or a Bruker-ARX-200 NMR apparatus from Bruker, tetramethylsilane being used as the internal standard. IR spectra were recorded with a Nicolet 510 P FT IR spectrometer. GC/MS data were obtained with a Finnigan MAT Magnum System 240 apparatus. Elemental analyses, where carried out, were carried out with a Perkin Elmer Elemental Analyser and gave adequate elemental analyses results: C±0.34, H±0.28, N±0.19.

General Working Instructions 1 (GWI 1; Imine+Iminium Salt Process)

The reactions were carried out under an argon atmosphere. A solution of the imine (VII) (2.5 mmol) in anhydrous $CH_2Cl_2$ (2.5 ml) was cooled to −80° C. The iminium salt (VIII) (2.5 mmol) was then added in one portion, while stirring. The mixture was stirred and the temperature was allowed to rise to −30° C. over 2-3 h. The reaction mixture was kept at this temperature in a deep-freeze for 15 h. $NaBH_4$ (40 mmol) in MeOH (10 ml) was then added and the temperature was allowed to rise to room temperature. After the mixture had been stirred for 5 hours at ambient temperature, HCl (5 ml, 6 N) was added and the mixture was washed a few times with $Et_2O$. The aqueous layer was then rendered alkaline by addition of $NH_3$ (25% $NH_3$:$H_2O$=1:1) and the diamine (I) according to the invention was extracted with $CH_2Cl_2$ (3×50 ml). The combined organic phases were dried over $Na_2SO_4$. The solvent was removed on a rotary evaporator and the residue was purified by means of column chromatography on $Al_2O_3$ ($CH_2Cl_2$/MeOH). The fraction eluted last was the diamine (I).

General Working Instructions 2 (GWI 2; Debenzylation of the Diamine (I) where $R^3$=—$CH_2$-phenyl)

A solution of the benzylated diamine (I) in anhydrous MeOH (10 ml) was stirred at room temperature in the presence of 10% Pd/C (20 mg), and $H_2$ was passed into the mixture until the debenzylation was complete (TLC control). After removal of the catalyst by means of filtration over Celite, the filtrate was evaporated to give the debenzylated diamine (I). The residue was purified by means of column chromatography on $Al_2O_3$ ($CH_2Cl_2$/MeOH=95:5).

General Working Instructions 3 (GWI 3; Azide Method)

Preparation of the Mannich Bases (III)

Dimethylamine hydrochloride (2.5 mmol), $NEt_3$ (5 mmol) and $Me_3SiCl$ (5.5 mmol) were added to a solution of anhydrous NaI (dried at 140° C. in vacuo) in dry MeCN (5.5 mmol; c≈1 mol/l). After the mixture had been stirred for 30 min at ambient temperature, the aldehyde A-CHO (2.5 mmol) was added and stirring was continued for a further 30 min. 1-(Pyrrolidino)-1-cyclohexene (2.5 mmol) was then added as the enamine and the mixture was stirred for a further 60 min. Thereafter, the mixture was acidified with aq. HCl (5 ml, 37% HCl:$H_2O$=1:1), stirred for 10 min and washed with $Et_2O$ (3×50 ml). Dilute $NH_3$ (25 ml, 25% $NH_3$:$H_2O$=1:4) were then added with vigorous stirring, and the Mannich base (III) was extracted with $CH_2Cl_2$ or $Et_2O$ (3×50 ml). The combined organic phases were dried over $Na_2SO_4$. Finally, the solvent was removed on a rotary evaporator without heating.

Preparation of the Amino-alcohols (IV)

The Mannich base (III) (1 mmol) was dissolved in ethanol (10 ml), $NaBH_4$ (2.5 mmol) was added and the mixture was stirred for 5 h at room temperature. Aq. HCl (37% HCl:$H_2O$=1:1, 10 ml) was then added and the mixture was washed a few times with $Et_2O$ (50 ml). The aqueous layer was rendered alkaline by addition of $NH_3$ (25% $NH_3$:$H_2O$=1:1). The product was extracted with $CH_2Cl_2$ (3×50 ml) and the organic phase was dried over $Na_2SO_4$. The solvent was removed in vacuo, to give a yellow oil. The product (IV) was used without further purification.

Mesylation of the Amino-alcohol (IV)

Mesyl chloride (2.4 mmol) and $NEt_3$ (3 mmol) were added to a solution of the amino-alcohol (IV) (2 mmol) in $CH_2Cl_2$ (5 ml). After 1 h the reaction was complete (TLC control). The mixture was diluted with $CH_2Cl_2$ (10 ml) and washed twice with aq. $Na_2CO_3$ solution and once with salt solution. The organic phase was dried with $Na_2SO_4$ to give the mesylate (V) as a yellow oil, which was employed in the following reactions without further purification.

Formation of the Azide (VI)

A solution of $NaN_3$ (20 mmol) and the mesylate (V) (2 mmol) in DMSO (40 ml) was heated at 50° C. for 3 h. The TLC showed complete consumption of the starting material. The reaction was quenched with salt solution and the mixture was extracted with $CH_2Cl_2$ (50 ml). The organic phase was washed three times with saturated $Na_2CO_3$ solution and once with salt solution. After drying over $Na_2SO_4$, the azide (VI) was obtained as a brown oil. The crude product (VI) was employed in the following reaction without further purification.

Reduction of the Azide (VI) to the Diamine (I)

A solution of the azide (VI) (1 mmol) in $Et_2O$ was added slowly to a suspension of $LiAlH_4$ (1.5 mmol) in $Et_2O$. After 4 h the reaction was quenched very slowly with water and HCl (37% HCl:$H_2O$=1:1). After being rendered alkaline, the product was extracted with $Et_2O$ (3×50 ml) and washed with water (50 ml). The organic phase was dried with $Na_2SO_4$ and chromatographed over $Al_2O_3$ ($CH_2Cl_2$/MeOH=95:5) to give the diamine (I) as a yellowish oil.

General Working Instructions 4 (GWI 4; Aminoimine (II) Reduction Process)

Variant (A)

A solution of ammonium acetate (12.1 mmol) and the Mannich base (III) (1.8 mmol) in THF were stirred for 1 h at room temperature. A solution of L-Selectride in THF (3.6 mmol) was added at 0° C., the temperature was allowed to rise to room temperature and stirring was continued overnight. HCl (5 ml, 6 N) was added and the mixture was washed a few times with $Et_2O$. The aqueous phase was then rendered alkaline with $NH_3$ (25% $NH_3$:$H_2O$=1:1) and the diamine (I) was extracted with $CH_2Cl_2$ (3×50 ml). The combined organic phases were dried over $Na_2SO_4$. The solvent was removed on a rotary evaporator and the residue was purified by means of column chromatography over $Al_2O_3$ ($CH_2Cl_2$/MeOH). The fraction eluted last was the diamine (I).

Variant B

A solution of ammonium acetate (12.1 mmol) and the Mannich base (III) (1.8 mmol) in THF was stirred for 1 h at room temperature. A solution of DIBAH in n-hexane (3.6 mmol) was added at 0° C. The temperature was allowed to rise to room temperature and stirring was continued overnight. HCl (5 ml, 6 N) was added and the mixture was washed a few times with $Et_2O$. The aq. phase was then rendered alkaline by addition of $NH_3$ (25% $NH_3$:$H_2O$=1:1) and the diamine (I) was extracted with $CH_2Cl_2$ (3×50 ml). The combined organic phases were dried over $Na_2SO_4$. The solvent was removed on a rotary evaporator and the residue was purified by means of column chromatography over $Al_2O_3$ ($CH_2Cl_2$/MeOH). The fraction eluted last was the diamine (I).

Variant C

NaCNBH$_3$ (2.1 mmol) was added to a suspension of ZnCl$_2$ in MeOH at 0° C. After the mixture had been stirred for 1 h at this temperature, the Mannich base (III) (1.8 mmol) and ammonium acetate (12.1 mmol) were added in one portion. The mixture was stirred and the temperature was allowed to rise to room temperature. Stirring was continued overnight. HCl (5 ml, 6 N) was added and the mixture was washed a few times with Et$_2$O. The aqueous phase was then rendered alkaline by addition of NH$_3$ (25% NH$_3$:H$_2$O=1:1) and the diamine (I) was extracted with CH$_2$Cl$_2$ (3×50 ml). The combined organic phases were dried over Na$_2$SO$_4$. The solvent was removed on a rotary evaporator and the residue was purified by means of column chromatography over Al$_2$O$_3$ (CH$_2$Cl$_2$/MeOH). The fraction eluted last was the diamine (I).

General Working Instructions 5 (GWI 5; Acylation Process)

The reaction vessel was thoroughly heated in a drying cabinet. The diamine (I) (where R$^3$=R$_4$=H) (600 mg) was initially introduced and a solution of 1.3 molar equivalents of triethylamine in methylene chloride (V/V=1:8), which contained a trace of 4-dimethylaminopyridine, was added. 1.3 molar equivalents of the acid chloride R$^7$—C(=O)—Cl were then added at −10° C. and the mixture was stirred overnight, while warming to room temperature. After renewed cooling to −10° C., 2 ml 5 N KOH solution were added, the phases were separated and the organic phase was washed again with 4 ml 0.1 N KOH solution. The organic phase was dried over magnesium sulfate and concentrated at 40° C. in vacuo. The crude product obtained was purified via MPLC (mobile phase n-hexane; gradual addition of diethyl ether up to 100%). The final precipitation of the hydrochloride was carried out by dissolving the crude base in approx. 10 ml 2-butanone per gram of base, subsequent addition of half a molar equivalent of water, followed by 1.1 molar equivalents of chlorotrimethylsilane, and stirring overnight. The hydrochloride which had precipitated out was filtered off and dried in vacuo.

General Working Instructions 6 (GWI 6; Hydrochloride Formation)

For precipitation of the hydrochloride, the crude base (I) was taken up in approx. 10 ml of 2-butanone per gram of base. 0.5 molar equivalent of water was then added, followed by 1.1 molar equivalents of chlorotrimethylsilane, and the mixture was stirred overnight. The hydrochloride which had precipitated out was filtered off and dried in vacuo.

The compounds prepared by way of example in accordance with GWI 1-6 are shown in table 1. The determination of the stereochemistry was carried out by means of $^1$H- and $^{13}$C-NMR analyses, in particular by comparison of the chemical shifts of the C atoms C—NR$^3$R$^4$, C—R$^1$ and C-A in the $^{13}$C-NMR spectrum of the compounds according to the invention with one another and with the shifts of the corresponding C atoms in the $^{13}$C-NMR spectrum of (anti,anti)-1-hydroxy-2-(pyrrolidin-phenyl-methyl)-cyclohexane and (syn,anti)-1-hydroxy-2-(pyrrolidin-phenyl-methyl)-cyclohexane.

TABLE 1

| Example no. | Compound | Preparation process (GWI) |
|---|---|---|
| 1 | (syn,syn)-N-[2-(dimethylaminopyridin-3-ylmethyl)cyclohexyl]benzamide hydrochloride | 4A/B + 5 + 6 |
| 1a | (syn,syn)-2-(dimethylaminopyridin-3-ylmethyl)cyclohexylamine | 4A/B |
| 2 | (syn,syn)-N-[2-(dimethylaminopyridin-3-ylmethyl)cyclohexyl]-2-fluorobenzamide hydrochloride | 4A/B + 5 + 6 |
| 3 | (syn,syn)-2-chloro-N-[2-(dimethylamino-pyridin-3-ylmethyl)cyclohexyl]-benzamide hydrochloride | 4A/B + 5 + 6 |
| 4 | (syn,syn)-N-[2-(dimethylaminopyridin-3-ylmethyl)cyclohexyl]-2-methylbenzamide hydrochloride | 4A/B + 5 + 6 |
| 5 | (anti,anti)-N-[2-(dimethylaminopyridin-3-ylmethyl)cyclohexyl]-benzamide hydrochloride | 4C + 5 + 6 |
| 5a | (anti,anti)-2-(dimethylaminopyridin-3-ylmethyl)cyclohexylamine | 4C |
| 6 | (anti,anti)-N-[2-(dimethylaminopyridin-3-ylmethyl)cyclohexyl]-2-fluorobenzamide hydrochloride | 4C + 5 + 6 |
| 7 | (anti,anti)-2-chloro-N-[2-(dimethylamino-pyridin-3-ylmethyl)cyclohexyl]benzamide hydrochloride | 4C + 5 + 6 |
| 8 | (anti,anti)-N-[2-(dimethylaminopyridin-3-ylmethyl)cyclohexyl]-2-methylbenzamide hydrochloride | 4C + 5 + 6 |
| 9 | (syn,syn)-N-[2-(dimethylaminopyridin-3-ylmethyl)cyclohexyl]acetamide hydrochloride | 4A/B + 5 + 6 |
| 10 | (anti,anti)-N-[2-(dimethylaminopyridin-3-ylmethyl)cyclohexyl]acetamide hydrochloride | 4C + 5 + 6 |
| 11 | (syn,syn)-N-[2-(dimethylaminophenyl-methyl)-cyclohexyl]-2-fluorobenzamide hydrochloride | 4A/B + 5 + 6 |
| 11a | (syn,syn)-2-(dimethylaminophenylmethyl)-cyclohexylamine | 4A/B |
| 12 | (syn,syn)-N-[2-(dimethylamino-phenyl-methyl)-cyclohexyl]-acetamide hydrochloride | 4A/B + 5 + 6 |
| 13 | (syn,syn)-N-[2-(dimethylamino-phenyl-methyl)-cyclohexyl]-benzamide hydrochloride | 4A/B + 5 + 6 |
| 14 | (syn,syn)-2-chloro-N-[2-(dimethylamino-phenyl-methyl)-cyclohexyl]-benzamide hydrochloride | 4A/B + 5 + 6 |
| 15 | (syn,syn)-N-[2-(dimethylamino-phenyl-methyl)-cyclohexyl]-2-methyl-benzamide hydrochloride | 4A/B + 5 + 6 |
| 16 | (anti,anti)-N-[2-(dimethylamino-phenyl-methyl)-cyclohexyl]-acetamide hydrochloride | 4C + 5 + 6 |
| 16a | (anti,anti)-2-(dimethylamino-phenyl-methyl)-cyclohexylamine | 4C |
| 17 | (anti,anti)-N-[2-(dimethylamino-phenyl-methyl)-cyclohexyl]-benzamide hydrochloride | 4C + 5 + 6 |
| 18 | (anti,anti)-N-[2-(dimethylamino-phenyl-methyl)-cyclohexyl]-2-methyl-benzamide hydrochloride | 4C + 5 + 6 |
| 19 | (syn,syn)-2-chloro-N-{2-[(2-chloro-phenyl)-dimethylamino-methyl]-cyclohexyl}-benzamide hydrochloride | 4A/B + 5 + 6 |
| 19a | (syn,syn)-2-[(2-chloro-phenyl)-dimethyl-aminomethyl]-cyclohexylamine | 4A/B |
| 20 | (anti,anti)-2-chloro-N-{2-[(2-chloro-phenyl)-dimethylamino-methyl]-cyclohexyl}-benzamide hydrochloride | 4C + 5 + 6 |
| 20a | (anti,anti)-2-[(2-chloro-phenyl)-dimethyl-aminomethyl]-cyclohexylamine | 4C |
| 21 | (syn,syn)-N-{2-[(2-chloro-phenyl)-dimethyl-aminomethyl]-cyclohexyl}-2-fluoro-benzamide hydrochloride | 4A/B + 5 + 6 |
| 22 | (anti,anti)-N-{2-[dimethylamino-(2-nitro-phenyl)-methyl]-cyclohexyl}-benzamide hydrochloride | 4C + 5 + 6 |

TABLE 1-continued

| Example no. | Compound | Preparation process (GWI) |
|---|---|---|
| 22a | (anti,anti)-2-[dimethylamino-(2-nitro-phenyl)-methyl]-cyclohexylamine | 4C |
| 23 | (anti,anti)-N-{2-[dimethylamino-(2-nitro-phenyl)-methyl]-cyclohexyl}-2-fluoro-benzamide hydrochloride | 4C + 5 + 6 |
| 24 | (anti,anti)-2-chloro-N-{2-[dimethylamino-(2-nitro-phenyl)-methyl]-cyclohexyl}-benzamide hydrochloride | 4C + 5 + 6 |
| 25 | (anti,anti)-N-{2-[dimethylamino-(2-nitro-phenyl)-methyl]-cyclohexyl}-2-methyl-benzamide hydrochloride | 4C + 5 + 6 |
| 26 | (syn,syn)-N-{2-[dimethylamino-(2-nitro-phenyl)-methyl]-cyclohexyl}-acetamide hydrochloride | 4A/B + 5 + 6 |
| 26a | (syn,syn)-N-2-[dimethylamino-(2-nitro-phenyl)-methyl]-cyclohexylamine | 4A/B |
| 27 | (anti,anti)-N-{2-[(2-chloro-phenyl)-dimethyl-amino-methyl]-cyclohexyl}-acetamide hydrochloride | 4C + 5 + 6 |
| 28 | (syn,anti)-2-(dimethylamino-phenyl-methyl)-cyclohexylamine | 1 + 2 |
| 29 | (syn,anti)-N-[2-(dimethylamino-phenyl-methyl)-cyclohexyl-benzamide | 1 |
| 30 | (anti,anti)-N-{2-[dimethylamino-(2-methoxy-phenyl)-methyl]-cyclohexyl}-benzamide | 4C + 5 |
| 30a | (anti,anti)-2-(dimethylamino-(2-methoxy-phenyl)-methyl]-cyclohexylamine | 4C |
| 31 | (anti,anti)-N-{2-[dimethylamino-(2-nitro-phenyl)-methyl]-cyclohexyl}-benzamide | 4C + 5 |
| 33 | (anti,anti)-N-{2-[(2-chloro-phenyl)-dimethyl-amino-methyl]-cyclohexyl}-benzamide | 4C + 5 |
| 35 | (anti,anti)-N-{2-[dimethylamino-(2-methoxy-phenyl)-methyl]-cyclohexyl}-acetamide | 4C + 5 |
| 36 | (anti,anti)-N-{2-[(2-chloro-phenyl)-dimethyl-amino-methyl]-cyclohexyl}-acetamide | 4C + 5 |
| 37 | (anti,anti)-N-{2-[dimethylamino-(2-nitro-phenyl)-methyl]-cyclohexyl}-acetamide | 4C + 5 |
| 38 | (syn,syn)-2-(dimethylamino-phenyl-methyl)-cyclohexylamine | 4A/B |
| 40 | (anti,anti)-2-chloro-N-(3-dimethylamino-1-ethyl-2-methyl-3-phenyl-propyl)-benzamide | 4C + 5 |
| 40a | (anti,anti)-3-dimethylamino-1-ethyl-2-methyl-3-phenyl-propylamine | 4C |
| 41 | (syn,anti)-2-(dimethylamino-phenyl-methyl)-cyclohexyl-N-(n-propyl)-amine | 1 |
| 42 | (syn,anti)-2-(morpholin-4-yl-phenyl-methyl)-cyclohexyl-N-(n-propyl)-amine | 1 |
| 43 | (syn,anti)-2,N,N-trimethyl-1,3-diphenyl-N'-propyl-propane-1,3-diamine | 1 |
| 44 | (syn,anti)-2-(dimethylamino-phenyl-methyl)-cyclohexyl-N-benzyl-amine | 1 |
| 45 | (syn,anti)-2-(morpholin-4-yl-phenyl-methyl)-cyclohexyl-N-benzyl-amine | 1 |
| 46 | (syn,anti)-2,N,N-trimethyl-1,3-diphenyl-N'-benzyl-propane-1,3-diamine | 1 |
| 47 | (syn,anti)-2-(dimethylamino-phenyl-methyl)-cyclohexylamine | 1 + 2; 3 |
| 48 | (syn,anti)-2-(moprholin-4-yl-phenyl-methyl)-cyclohexylamine | 1 + 2 |
| 49 | (syn,anti)-2,N,N-trimethyl-1,3-diphenyl-propane-1,3-diamine | 1 + 2 |
| 50 | (syn,anti)-2-[(2-chlorophenyl)-dimethyl-amino-methyl]-cyclohexylamine | 3 |
| 51 | (anti,anti)-2-[(2-chlorophenyl)-dimethyl-amino-methyl]-cyclohexylamine | 4C |
| 52 | (syn,syn)-2-(dimethylamino-phenyl-methyl)-cyclohexylamine | 4A/B |
| 53 | (anti,anti)-2-(dimethylamino-phenyl-methyl)-cyclohexylamine | 4C |
| 54 | (syn,syn)-2-[(2-chlorophenyl)-dimethyl-amino-methyl]-cyclohexylamine | 4A/B |
| 55 | (syn,syn)-2-(dimethylamino-pyridin-3-yl-methyl)-cyclohexylamine | 4A/B |
| 56 | (anti,anti)-2-(dimethylamino-pyridin-3-yl-methyl)-cyclohexylamine | 4C |
| 57 | (syn,syn)-2-(dimethylamino-(2-methoxy-phenyl)-methyl)-cyclohexylamine | 4A/B |
| 58 | (anti,anti)-2-(dimethylamino-(2-methoxy-phenyl)-methyl)-cyclohexylamine | 4C |
| 59 | (syn,syn)-2-(dimethylamino-(2-nitrophenyl)-methyl)-cyclohexylamine | 4A/B |
| 60 | (anti,anti)-2-(dimethylamino-(2-nitrophenyl)-methyl)-cyclohexylamine | 4C |

Spectroscopic Data

The spectroscopic data of some selected compounds given as examples are shown in tables 2 to 5.

TABLE 2

| Example no. | $^1$H NMR (CDCl$_3$)/TMS δ [ppm], J [Hz] | $^{13}$C NMR (CDCl$_3$)/TMS δ [ppm] | IR ν [cm$^{-1}$] |
|---|---|---|---|
| 44 | 0.74–0.83 (m, 1 H, ]-(CH$_2$)$_4$-[), 1.07–1.28 (m, 3 H, ]-(CH$_2$)$_4$-[), 1.57–1.70 (m, 3 H, ]-(CH$_2$)$_4$-[), 1.94–2.09 (m, 1 H, CHCHCH), 2.12 (6 H, N(CH$_3$)$_2$), 2.14–2.20 (m, 1 H, ]-(CH$_2$)$_4$-[), 2.29–2.36 (m, 1 H, CHCHCH), 3.65 (d, 1 H, J = 12.8, PhCH), AB-System (δ$_A$ = 3.65, δ$_B$ = 3.95, J = 12.8, CH$_2$Ph), 7.11–7.40 (m, 10 H, Ar—H). | 24.41, 25.42, 27.49, 31.68 (t, ]-(CH$_2$)$_4$-[), 41.42 (d, CHCHCHPh), 42.23 (q, N(CH$_3$)$_2$), 50.75 (t, CH$_2$Ph), 60.44 (d, CHCHCHPh), 73.79 (d, CHPh), 126.50, 126.52, 127.31, 128.01, 128.17, 129.33 (d, CH), 136.36, 141.00 (s, C). | 3444, 1635, 1557, 1452, 1028, 744, 698. |
| 45 | 0.62–2.36 (m, 14 H, ]-(CH$_2$)$_4$-[, CHCHCHPh, CHCHCH—Ph, ]-CH$_2$—N—CH$_2$-[), 3.36–3.97 (m, 7 H, CH$_2$Ph, ]-CH$_2$—O—CH$_2$-[, CHPh), 7.11–7.37 (m, 10 H, Ar—H). | 25.04, 26.31, 29.49, 33.96 (t, ]-(CH$_2$)$_4$-[), 48.13 (d, CHCHCHPh), 51.54, 52.18 (t, ]-CH$_2$—N—CH$_2$-[, CH$_2$Ph), 61.83 (d, CHCHCHPh), 67.32 (t, —CH$_2$—O—CH$_2$—), 67.40 (d, CHPh), 127.25, 128.57, 128.63, 128.71, 128.86 (d, CH), 141.34, 143.13 (s, C). | 3446, 2924, 2852, 1627, 1451, 1383, 1251, 1106, 1070, 700. |
| 46 | 0.53 (d, 3 H, J = 6.8 Hz, CHCH$_3$), 2.19 (s, 6 H, N(CH$_3$)$_2$), 2.46–2.65 (m, 1 H, CHCH$_3$), 3.23 (d, 1 H, J = 9.4, PhCH), AB-System (δ$_A$ = 3.57, δ$_B$ = 3.71, J = 13.1, CH$_2$Ph), 3.93 (d, 1 H, J = 6.3, PhCH), 7.13–7.52 (15 H, Ar—H). | 13.58 (t, CH$_3$CH), 39.37 (d, CH$_3$CH), 42.05 (q, N(CH$_3$)$_2$), 52.19 (t, CH$_2$Ph), 64.80, 73.07 (d, PhCH), 127.18, 127.97, 128.36, 128.70, 128.77, 128.98, 129.10, 129.93 (d, CH), 136.48, 141.56, 142.63 (s, C). | 3025, 2940, 2791, 1605, 1476, 1444, 1365, 1073, 1028, 754. |

TABLE 3

| Example no. | $^1$H NMR (CDCl$_3$)/TMS δ [ppm], J [Hz] | $^{13}$C NMR (CDCl$_3$)/TMS δ [ppm] | IR ν [cm$^{-1}$] |
|---|---|---|---|
| 47 | 0.70–1.89 (m, 9 H, ]-(CH$_2$)$_4$-[, | 24.90, 25.13, 30.23, 31.83, (t, ]-(CH$_2$)$_4$-[), | 3339, 2955, 2852, 2868, |

TABLE 3-continued

| Example no. | 1H NMR (CDCl3)/TMS δ [ppm], J [Hz] | 13C NMR (CDCl3)/TMS δ [ppm] | IR ν [cm⁻¹] |
|---|---|---|---|
|  | CHCHCHPh), 2.16 (s, 6 H, N(CH3)2), 2.43–2.53 (m, 1 H, CHCHCHPh), 3.40 (d, 1 H, J = 10.9, CHPh), 7.09–7.42 (m, 5 H, Ar—H). | 38.17 (q, N(CH3)2), 45.13 (d, CHCHCHPh), 57.94 (d, CHCHCHPh), 76.65 (d, CHPh), 127.26, 128.03, 129.83 (d, CH), 137.29 (s, C). | 1557, 1458, 1452, 1381. |
| 48 | 0.40–2.60 (m, 13 H, ]-(CH2)4-[, CHCHCHPh, ]-CH2—N—CH2-[), 3.16–3.98 (m, 5 H, ]-CH2—O—CH2-[, CHCHCHPh), 4.19 (d, 1 H, J = 10.0, CHPh), 7.21–7.56 (m, 5 H, Ar—H). | 25.41, 26.11, 27.26, 37.45 (t, ]-(CH2)4-[), 44.34 (d, CHCHCH), 51.56 (t, ]-CH2—N—CH2-[), 54.22 (d, CHCHCHPh), 67.40 (t, ]-CH2—O—CH2[), 67.71 (d, CHPh), 126.83, 127.41, 128.15, 128.59, 129.85 (d, CH), 137.56 (s, C). | 3440, 2921, 2852, 1652, 1456, 1448, 1384, 1113, 1031, 703. |
| 49 | 0.48 (d, 3 H, J = 6.8, CHCH3), 2.15 (s, 6 H, N(CH3)2), 2.65–2.41 (m, 1 H, CHCH3), 3.13 (d, 1 H, J = 9.4, N(CH3)2CH), 4.14 (d, 1 H, J = 6.0, CHNH2), 7.09–7.42 (m, 10 H, Ar—H). | 13.00 (q, CHCH3), 40.75 (d, CHCH3), 42.16 (q, N(CH3)2), 57.84 (d, N(CH3)2CH), 72.94 (d, NH2CH), 127.09, 127.27, 128.03, 128.13, 128.37, 129.89 (d, CH), 136.54, 145.08 (s, C). | 2950, 2929, 2858, 1729, 1452, 1383, 1185, 1029. |
| 50 | 0.60–2.06 (m, 9 H, ]-(CH2)4-[, CHCHCHPh), 2.50 (s, 6 H, N(CH3)2), 3.10–3.19 (m, 2 H, CHPh, CHCHCHPh), 7.08–7.51 (m, 4 H, Ar—H). | 25.01, 25.69, 30.01, 31.65 (t, ]-(CH2)4-[), 38.34 (q, N(CH3)2), 43.47 (d, CHCHCHPh), 69.72 (d, CHPh), 77.98 (d, CHCHCHPh), 127.22, 128.83, 128.95, 129.35 (d, CH), 133.27, 135.66 (s, C). | 3430, 2929, 1635, 1438, 1062, 750. |
| 51 | 0.60–2.06 (m, 9 H, ]-(CH2)4-[, CHCHCHPh), 2.50 (s, 6 H, N(CH32), 3.10–3.19 (m, 2 H, CHPh, CHCHCHPh), 7.08–7.51 (m, 4 H, Ar—H). | 25.01, 25.69, 30.01, 31.65 (t, ]-(CH2)4-[), 38.34 (q, N(CH3)2), 43.47 (d, CHCHCHPh), 69.72 (d, CHPh), 77.98 (d, CHCHCHPh), 127.22, 128.83, 128.95, 129.35 (d, CH), 133.27, 135.66 (s, C). |  |

TABLE 4

| Example no. | 1H NMR (CDCl3)/TMS δ [ppm], J [Hz] | 13C NMR (CDCl3)/TMS δ [ppm] | IR ν [cm⁻¹] | MS (70 eV) m/z [%] |
|---|---|---|---|---|
| 52 | 0.96–2.13 (m, 8 H, ]-(CH2)4-[, CHCHCHPh), 2.17 (s, 6 H, N(CH3)2), 2.25–2.60 (m, 1 H, CHCHCHPh), 3.74–4.06 (m, 2 H, CHCHCHPh, CHPh), 7.09–7.53 (m, 5 H, Ar—H). | 21.86, 24.22, 27.45, 32.40 37 (t, -]CH2)4-[), 37.96 (d, CHCHCHPh), 41.25 (q, N(CH3)2), 68.97 CHCHCHPh), 71.90 (d, CHPh), 127.85, 128.26, 130.24 (d, CH), 136.86 (s, C). | 3405, 2929, 2857, 2782, 1450, 1384, 1068, 975, 752, 703. | 232 [M⁺] (13), 134 (100), 118 (5), 91 (9), 77 (3). |
| 54 | 0.96–1.88 (m, 8 H, ]-(CH2)4-[), 2.23 (s, 6 H, N(CH3)2), 2.31–2.56 (m, 1 H, CHCHCH), 3.94–4.03 (m, 1 H, CHCHCHPh), 4.90 (d, 1 H, J = 11.6, CHPh), 7.20–7.48 (m, 4 H, Ar—H). | 21.76, 24.63, 27.70, 32.37 (t, ]-(CH2)4-[), 38.50 (d, CHCHCHPh), 41.49 (q, N(CH3)2), 62.27 (CHCHCHPh), 72.56 (d, CHPh), 126.42, 128.88, 130.41, 130.56 (d, CH), 132.68, 136.42 (s, C). | 3434, 2929, 2859, 2782, 1643. 1463, 1062. 1035. 975, 754. | 267 [M⁺] (53), 167 (100), 130 (7). |
| 55 | 0.89–1.87 (m, 8 H, ]-(CH2)4-[), 2.13 (s, 6 H, N(CH3)2), 2.42–2.54 (m, 1 H, CHCHCH), 3.71–4.02 (m, 2 H, CHCHCHPh, CHPh), 7.29–7.49 (m, 2 H, Ar—H), 8.41–8.56 (m, 2 H, Ar—H). | 22.10, 23.72, 27.12, 32.33 (t, ]-(CH2)4-[), 38.10 (d, CHCHCHPh), 41.16 (q, N(CH3)2), 66.79 (CHCHCHPh), 71.13 (d, CHPh), 123.43 (d, CH), 128.90 (s, C), 137.13, 149.33, 151.32 (d, CH). | 3417, 2927, 2857, 1646, 1062, 1029, 977. | 235 [M⁺ + 1] (2), 217 (2), 164 (5), 135 (100), 119 (4), 92 (2). |
| 57 | 0.95–1.94 (m, 8 H, ]-(CH2)4-[), 2.15 (s, 6 H, N(CH3)2), 2.48–2.56 (m, 1 H, CHCHCHPh), 3.73–4.00 (m, 2 H, CHCHCHPh, CHPh), 3.83 (s, 3 H, OMe), 6.94–7.01 (m, 2 H, Ar—H), 7.12 (d, 1 H, J = 7.5, Ar—H), 7.28–7.33 (m, 1 H, Ar—H). | 21.43, 24.92, 27.97, 32.32 (t, ]-(CH2)4-[), 38.02 (d, CHCHCHPh), 41.42 (q, N(CH3)2), 55.87 (CHCHCHPh), 73.01 (d, CHPh), 111.30, 120.11, 122.38 (s, C), 128.64, 129.65 43 (d, CH), 158.98 (s, C). | 3426, 2927, 2857, 2784, 1068, 975, 752, 703. | 263 [M⁺ + 1], (3), 218 (2), 164 (100), 148 (12), 121 (7), 91 (8). |
| 59 | 0.81–1.91 (m, 8 H, ]-(CH2)4-[, CHCHCH), 1.98 (s, 6 H, N(CH3)2), 2.20–2.46 (m, 2 H, CHCHCHPh), 3.51–3.69 (m, 1 H, CHCHCHPh), 4.73 (d, 1 H, J = 11.3, CHPh), 7.29–7.41 (m, 2 H, Ar—H), 7.51–7.59 (m, 1 H, Ar—H), 7.69 (d, 1 H, J = 8.0). | 22.70, 23.41, 25.92, 32.55 (t, ]-(CH2)4-[), 39.03 (d, CHCHCHPh), 40.99 (q, N(CH3)2), 60.88 (d, CHCHCHPh), 70.51 (d, CHPh), 124.42 (d, CH), 127.92 (s, C), 128.37, 130.27, 131.56 (d, CH), 152.76 (s, C). | 3417, 2931, 2859, 1527, 1455, 1068, 977. | 277 [M⁺] (12), 261 (3), 179 (100), 132 (37), 91 (5). |

TABLE 5

| Example no. | 1H NMR (CDCl3)/TMS δ [ppm], J [Hz] | 13C NMR (CDCl3)/TMS δ [ppm] | IR ν [cm⁻¹] | MS (70 eV) m/z [%] |
|---|---|---|---|---|
| 53 | 0.53–2.50 (m, 9 H, ]-(CH2)4-[, CHCHCH), 2.17 (s, 6 H, N(CH3)2), 3.41–3.76 (m, 2 H, | 25.03, 26.20, 29.29, 35.37 (t, ]-(CH2)4-[), 41.32 (d, CHCHCHPh), 42.75 (q, | 3421, 2929, 2857, 2782, 1450, 1384, 1062, 1043, 1033, 975. | 232 [M⁺] (19), 134 (100), 91 (9), 77 (3). |

TABLE 5-continued

| Example no. | $^1$H NMR (CDCl$_3$)/TMS δ [ppm], J [Hz] | $^{13}$C NMR (CDCl$_3$)/TMS δ [ppm] | IR ν [cm$^{-1}$] | MS (70 eV) m/z [%] |
|---|---|---|---|---|
|  | CHCHCHPh, CHPh), 7.08–7.44 (m, 5 H, Ar—H). | N(CH$_3$)$_2$), 76.60 (CHCHCHPh), 78.00 (d, CHPh), 127.79, 128.17 (d, CH), 137.45 (s, C). |  |  |
| 56 | 0.57—2.07 (m, 9 H, ]-(CH$_2$)$_4$-[, CHCHCH), 2.14 (s, 6 H, N(CH$_3$)$_2$), 3.44– 3.63 (m, 2 H, CHCHCHPh, CHPh), 7.29–7.56 (m, 2 H, Ar—H), 8.35–8.54 (m, 2 H, Ar—H). | 24.83, 26.03, 29.22, 35.19 (t, ]-(CH$_2$)$_4$-[), 41.22 (q, N(CH$_3$)$_2$), 42.47 (d, CHCHCHPh), 74.10 (CHCHCHPh), 77.77 (d, CHPh), 123.37 (d, CH), 129.63 (s, C), 136.83, 149.32, 151.24 (d, CH). | 3421, 2929, 2857, 1445, 1384, 1070, 1043, 977. | 234 [M$^+$], 164 (5), 135 (100), 91 (5). |
| 58 | 0.61–2.52 (m, 9 H, ]-(CH$_2$)$_4$-[, CHCHCH), 2.17 (s, 6 H, N(CH$_3$)$_2$), 3.48– 3.69 (m, 1 H, CHCHCHPh, 3.83 (s, 3 H, OCH$_3$), 4.40 (d, 1 H, J = 11.1, CHPh), 6.92–7.30 (m, 4 H, Ar—H). | 25.08, 26.22, 28.87, 35.38 (t, ]-(CH$_2$)$_4$-[), 41.59 (d, CHCHCHPh), 42.93 (q, N(CH$_3$)$_2$), 55.76 (q, OCH$_3$), 65.42 (CHCHCHPh), 77.98 (d, CHPh), 110.70, 120.40 (d, CH), 122.75 (s, C), 127.99, 130.82 (d, CH), 159.16 (s, C). | 3423, 2934, 2857, 2784, 1068, 975, 752, 703. | 262 [M$^+$] (3), 164 (100), 148 (20), 121 (10), 91 (6). |
| 60 | 0.92–2.49 (m, 9 H,]-(CH$_2$)$_4$-[), CHCHCH), 2.07 (s, 6 H, N(CH$_3$)$_2$), 3.63– 3.73 (m, 1 H, CHCHCHPh), 4.42 (d, 1 H, J = 10.6 Hz, CHPh), 7.33–7.81 (m, 4 H, Ar—H). | 24.75, 26.03, 28.42. 35.11 (t, ]-(CH$_2$)$_4$-[), 41.40 (q, N(CH$_3$)$_2$), 43.02 (d, CHCHCHPh), 67.78 (CHCHCHPh), 77.54 (d, CHPh), 124.41, 128.54, 129.37 (s, C), 130.54, 131.81 (d, CH), 152.45 (s, C). | 3415, 2936, 2864, 1523, 1455, 1068, 977. | 277 [M$^+$] (20), 179 (100), 132 (37), 91 (30). |

Pharmacological Studies

Testing of Analgesia in the Writhing Test in the Mouse

The investigation for analgesic activity was carried out in the phenylquinone-induced writhing in the mouse (modified by I. C. Hendershot and J. Forsaith (1959) J. Pharmacol. Exp. Ther. 125, 237-240). Male NMRI mice weighing 25 to 30 g were employed for this. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of the test substances. The animals were placed individually in observation cages. The number of pain-induced stretching movements (so-called writhing reactions=straightening of the body with stretching of the hind extremities) was counted by means of a push-button counter 5 to 20 minutes after the administration of phenylquinone. Animals which received only physiological saline solution were also run as a control. All the substances were tested in the standard dosage of 10 mg/kg. The percentage inhibition (% inhibition) of the writhing reaction by a substance was calculated according to the following formula:

$$\% \text{ inhibition} = 100 - \frac{\text{writhing reactions of the treated animals}}{\text{writhing reactions of the control animals}} * 100$$

All the compounds according to the invention investigated showed a pronounced analgesic action. The results are summarised in the following table 6.

TABLE 6

| Example no. | % Inhibition of the writhing reaction (dosage in mg/kg intravenously) |
|---|---|
| 1 | 54 (10) |
| 2 | 67 (10) |
| 3 | 85 (10) |
| 4 | 34 (10) |
| 5 | 49 (10) |
| 6 | 62 (10) |
| 7 | 56 (10) |
| 8 | 40 (10) |
| 9 | 75 (10) |
| 10 | 59 (10) |

Pharmaceutical Formulation of a Medicament According to the Invention 1 g of the hydrochloride of (syn,syn)-2-chloro-N-[2-(dimethylaminopyridin-3-ylmethyl)cyclohexyl]-benzamide was dissolved in 1 l of water for injection purposes at room temperature and the solution was then adjusted to isotonic conditions by addition of sodium chloride.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula (I)

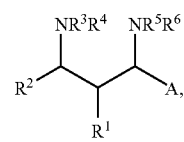

or a pharmaceutically acceptable salt thereof,
wherein
R$^1$ and R$^2$ together are —(CH$_2$)$_m$— and form a ring in combination with the carbons to which R$^1$ and R$^2$ are connected in formula (I), where m=2, 3, 4, 5 or 6, wherein the —(CH$_2$)$_m$— ring is optionally substituted one or more times by C$_{1-6}$-alkyl, aryl, O—C$_{1-6}$-alkyl, O—(C$_{1-6}$-alkyl)-aryl, or benzo-fused;
R$^3$ is selected from the group consisting of H, C$_{1-12}$-alkyl, C$_{3-8}$-cycloalkyl, aryl, —(C$_{1-6}$-alkyl)-C$_{3-8}$-cycloalkyl, —($C_{1-6}$-alkyl)-aryl, heterocyclyl, —($C_{1-6}$-alkyl)-heterocyclyl, and C(=O)—$R^7$, $R^4$ is selected from the group consisting of H, $C_{1-12}$-alkyl, $C_{3-8}$-cycloalkyl, aryl, —($C_{1-6}$-alkyl)-$C_{3-8}$-cycloalkyl, —($C_{1-6}$-alkyl)-aryl, heterocyclyl, and —($C_{1-6}$-alkyl)-heterocyclyl, $R^5$ and $R^6$ are independently selected from the group consisting of $C_{1-12}$-alkyl, $C_{3-8}$-cycloalkyl, aryl, —($C_{1-6}$-alkyl)-$C_{3-8}$-cycloalkyl, and ($C_{1-6}$-alkyl)-aryl, and A is selected from the group consisting of aryl, heteroaryl, C(=O)$OR^{10}$, and 2-propyl;

wherein $R^7$ is selected from the group consisting of $C_{1-6}$-alkyl, $C_{3-8}$-cycloalkyl, aryl, heterocyclyl, —($C_{1-6}$-alkyl)-$C_{3-8}$-cycloalkyl, —($C_{1-6}$-alkyl)-aryl, and —($C_{1-6}$-alkyl)-heterocyclyl;

$R^{10}$ is selected from the group consisting of $C_{1-6}$-alkyl, $C_{3-8}$-cycloalkyl, aryl, —($C_{1-6}$-alkyl)-$C_{3-8}$-cycloalkyl, and —($C_{1-6}$-alkyl)-aryl;

wherein the compound corresponding to formula (I) is present as a racemate or in the form of one or more diastereomers or one or more enantiomers;

and wherein the compound corresponding to formula (I) is not selected from benzyl-[2-(dimethylamino-phenyl-methyl)-cyclohexyl]-amine.

2. A compound according to claim 1, wherein $R^1$ and $R^2$ together are —$(CH_2)_m$— and form a ring in combination with the carbons to which $R^1$ and $R^2$ are connected in formula (I), where m=3, 4 or 5;

$R^3$ is selected from the group consisting of H, $C_{1-6}$-alkyl, aryl, —($C_{1-6}$-alkyl)-aryl, heteroaryl, and C(=O)—$R^7$, $R^4$ is selected from the group consisting of H, $C_{1-6}$-alkyl, aryl, —($C_{1-6}$-alkyl)-aryl, and heteroaryl, and $R^5$ and $R^6$ are independently selected from the group consisting of $C_{1-6}$-alkyl, aryl, and ($C_{1-6}$-alkyl)-aryl, wherein $R^7$ is selected from the group consisting of $C_{1-6}$-alkyl, aryl, —($C_{1-6}$-alkyl)-aryl, heteroaryl, and —($C_{1-6}$-alkyl)-heteroaryl;

$R^{10}$ is selected from the group consisting of $C_{1-6}$-alkyl, aryl, and —($C_{1-6}$-alkyl)-aryl; and aryl is a radical selected from the group consisting of

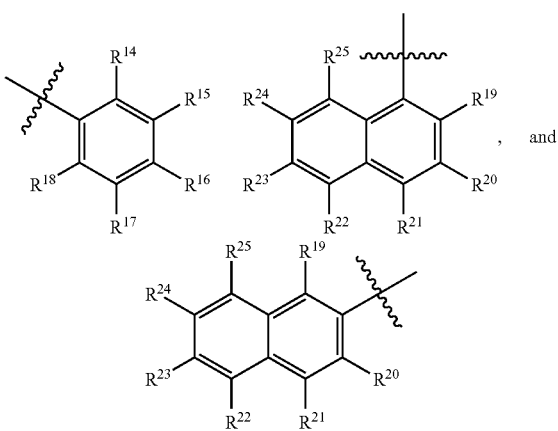

where $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are independently selected from the group consisting of H, $C_{1-6}$-alkyl, F, Cl, Br, I, $CF_3$, $OR^{11}$, $OCF_3$, $SR^{12}$, $SO_2CH_3$, $SO_2CF_3$, phenyl, CN, $CO_2R^{13}$, and $NO_2$; and $R^{11}$, $R^{12}$ and $R^{13}$ are independently selected from the group consisting of H, $C_{1-6}$-alkyl, phenyl, benzyl, and phenethyl.

3. A compound according to claim 1, wherein $R^1$ and $R^2$ together are —$(CH_2)_m$— and form a ring in combination with the carbons to which $R^1$ and $R^2$ are connected in formula (I), where m=3 or 4;

$R^3$ is selected from the group consisting of H, methyl, ethyl, n-propyl, 2-propyl, n-butyl, iso-butyl, sec-butyl, tert-butyl, phenyl, —$CH_2$-$aryl^1$, and C(=O)—$R^7$, $R^4$ is selected from the group consisting of H, methyl, ethyl, n-propyl, 2-propyl, n-butyl, iso-butyl, sec-butyl, tert-butyl, phenyl, and —$CH_2$-$aryl^3$, $R^5$ and $R^6$ are independently selected from the group consisting of methyl, ethyl, n-propyl, 2-propyl, and —$CH_2$-phenyl, A is selected from the group consisting of $aryl^4$, pyridinyl which is optionally substituted one or more times, C(=O)$OR^{10}$, and 2-propyl;

wherein $R^7$ is selected from the group consisting of methyl, ethyl, n-propyl, 2-propyl, n-butyl, iso-butyl, sec-butyl, tert-butyl, and $aryl^2$;

$R^{10}$ is selected from the group consisting of methyl, ethyl, n-propyl, 2-propyl, n-butyl, tert-butyl, and benzyl; and $aryl^1$, $aryl^2$, $aryl^3$, and $aryl^4$ independently of one another are

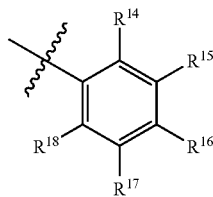

wherein 2, 3, 4 or 5 of the radicals $R^{14}$, $R^{15}$, $R^{16}$, $R^{17}$, and $R^{18}$ are H, and the other radicals of $R^{14}$, $R^{15}$, $R^{16}$, $R^{17}$, and $R^{18}$ are independently selected from the group consisting of H, $C_{1-6}$-alkyl, F, Cl, Br, I, $CF_3$, $OR^{11}$, $OCF_3$, $SR^{12}$, $SO_2CH_3$, $SO_2CF_3$, phenyl, CN, $CO_2R^{13}$, and $NO_2$, and wherein $R^{11}$, $R^{12}$, and $R^{13}$ are independently selected from the group consisting of H, $C_{1-6}$-alkyl, phenyl, benzyl, and phenethyl.

4. A compound according to claim 1, wherein $R^1$ and $R^2$ together are —$(CH_2)_4$— and form a ring in combination with the carbons to which $R^1$ and $R^2$ are connected in formula (I);

$R^3$ is selected from the group consisting of H, n-propyl, —$CH_2$-phenyl, and C(=O)—$R^7$;

$R^4$ is H;

$R^5$ and $R^6$ are each methyl;

A is selected from the group consisting of phenyl, 2-chlorophenyl, 2-methoxyphenyl, 2-nitrophenyl, and pyridin-3-yl; and $R^7$ is selected from the group consisting of methyl, phenyl, 2-fluorophenyl, 2-chlorophenyl, and 2-methylphenyl.

5. A compound according to claim 1, wherein the compound corresponding to formula (I) or a pharmaceutically acceptable salt thereof is present as a diastereomer of the formula (syn,anti-I)

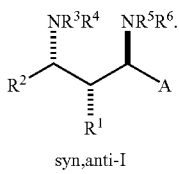

syn,anti-I

6. A compound according to claim 5, wherein the compound corresponding to formula (I) or a pharmaceutically acceptable salt thereof is present in an enantiomerically pure form.

7. A compound according to claim 1, wherein the compound corresponding to formula (I) or a pharmaceutically acceptable salt thereof is present as a diastereomer of the formula (anti,anti-I)

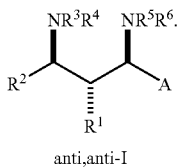

anti,anti-I

8. A compound according to claim 7 wherein the compound corresponding to formula (I) or a pharmaceutically acceptable salt thereof is present in an enantiomerically pure form.

9. A compound according to claim 1 wherein the compound corresponding to formula (I) or a pharmaceutically acceptable salt thereof is present as a diastereomer of the formula (anti,syn-I)

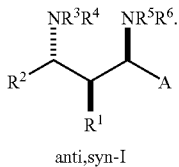

anti,syn-I

10. A compound according to claim 9, wherein the compound corresponding to formula (I) or a pharmaceutically acceptable salt thereof is present in an enantiomerically pure form.

11. A compound according to claim 1 wherein the compound corresponding to formula (I) or a pharmaceutically acceptable salt thereof is present as a diastereomer of the formula (syn,syn-I)

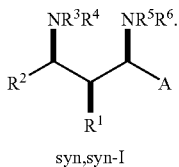

syn,syn-I

12. A compound according to claim 11, wherein the compound corresponding to formula (I) or a pharmaceutically acceptable salt thereof is present in an enantiomerically pure form.

13. A compound according to claim 1, wherein the compound is selected from the group consisting of:
(syn,syn)-N-[2-(dimethylaminopyridin-3-ylmethyl)cyclohexyl]-benzamide or its hydrochloride
(syn,syn)-2-(dimethylaminopyridin-3-ylmethyl)cyclohexylamine or its hydrochloride
(syn,syn)-N-[2-(dimethylaminopyridin-3-ylmethyl)cyclohexyl]-2-fluorobenzamide or its hydrochloride
(syn,syn)-2-chloro-N-[2-(dimethylaminopyridin-3-ylmethyl)cyclohexyl]-benzamide or its hydrochloride
(anti,anti)-N-[2-(dimethylaminopyridin-3-ylmethyl)cyclohexyl]-benzamide or its hydrochloride
(anti,anti)-2-(dimethylaminopyridin-3-ylmethyl)cyclohexylamine or its hydrochloride
(anti,anti)-N-[2-(dimethylaminopyridin-3-ylmethyl)cyclohexyl]-2-fluorobenzamide or its hydrochloride
(anti,anti)-2-chloro-N-[2-(dimethylaminopyridin-3-ylmethyl)cyclohexyl]benzamide or its hydrochloride
(anti,anti)-N-[2-(dimethylaminopyridin-3-ylmethyl)cyclohexyl]-2-methylbenzamide or its hydrochloride
(syn,syn)-N-[2-(dimethylaminopyridin-3-ylmethyl)cyclohexyl]-2-methylbenzamide or its hydrochloride
(syn,syn)-N-[2-(dimethylaminopyridin-3-ylmethyl)cyclohexyl]acetamide or its hydrochloride
(anti,anti)-N-[2-(dimethylaminopyridin-3-ylmethyl)cyclohexyl]acetamide or its hydrochloride
(syn,syn)-N-[2-(dimethylaminophenylmethyl)cyclohexyl]-2-fluorobenzamide or its hydrochloride
(syn,syn)-2-(dimethylaminophenylmethyl)cyclohexylamine or its hydrochloride
(syn,syn)-N-[2-(dimethylamino-phenyl-methyl)-cyclohexyl]-acetamide or its hydrochloride
(syn,syn)-N-[2-(dimethylamino-phenyl-methyl)-cyclohexyl]-benzamide or its hydrochloride
(syn,syn)-2-chloro-N-[2-(dimethylamino-phenyl-methyl)-cyclohexyl]-benzamide or its hydrochloride
(syn,syn)-N-[2-(dimethylamino-phenyl-methyl)-cyclohexyl]-2-methyl-benzamide or its hydrochloride
(anti,anti)-N-[2-(dimethylamino-phenyl-methyl)-cyclohexyl]-acetamide or its hydrochloride
(anti,anti)-2-(dimethylamino-phenyl-methyl)-cyclohexylamine or its hydrochloride
(anti,anti)-N-[2-(dimethylamino-phenyl-methyl)-cyclohexyl]-benzamide or its hydrochloride
(anti,anti)-N-[2-(dimethylamino-phenyl-methyl)-cyclohexyl]-2-methyl-benzamide or its hydrochloride
(syn,syn)-2-chloro-N-{2-[(2-chloro-phenyl)-dimethylamino-methyl]-cyclohexyl}-benzamide or its hydrochloride
(syn,syn)-2-[(2-chloro-phenyl)-dimethylamino-methyl]-cyclohexylamine or its hydrochloride
(anti,anti)-2-chloro-N-{2-[(2-chloro-phenyl)-dimethylamino-methyl]-cyclohexyl}-benzamide or its hydrochloride
(anti,anti)-2-[(2-chloro-phenyl)-dimethylamino-methyl]-cyclohexylamine or its hydrochloride
(syn,syn)-N-{2-[(2-chloro-phenyl)-dimethylamino-methyl]-cyclohexyl}-2-fluoro-benzamide or its hydrochloride
(anti,anti)-N-{2-[dimethylamino-(2-nitro-phenyl)-methyl]-cyclohexyl}-benzamide or its hydrochloride
(anti,anti)-2-[dimethylamino-(2-nitro-phenyl)-methyl]-cyclohexylamine or its hydrochloride
(anti,anti)-N-{2-[dimethylamino-(2-nitro-phenyl)-methyl]-cyclohexyl}-2-fluoro-benzamide or its hydrochloride (anti,anti)-2-chloro-N-{2-[dimethylamino-(2-nitro-phenyl)-methyl]-cyclohexyl}-benzamide or its hydrochloride
(anti,anti)-N-{2-[dimethylamino-(2-nitro-phenyl)-methyl]-cyclohexyl}-2-methyl-benzamide or its hydrochloride
(syn,syn)-N-{2-[dimethylamino-(2-nitro-phenyl)-methyl]-cyclohexyl}-acetamide or its hydrochloride
(syn,syn)-N-2-[dimethylamino-(2-nitro-phenyl)-methyl]-cyclohexylamine or its hydrochloride
(anti,anti)-N-{2-[(2-chloro-phenyl)-dimethylamino-methyl]-cyclohexyl}-acetamide or its hydrochloride
(syn,anti)-2-(dimethylamino-phenyl-methyl)-cyclohexylamine
(syn,anti)-N-[2-(dimethylamino-phenyl-methyl)-cyclohexyl]-benzamide
(anti,anti)-N-{2-[dimethylamino-(2-methoxy-phenyl)-methyl]-cyclohexyl}-benzamide
(anti,anti)-N-{2-[dimethylamino-(2-nitro-phenyl)-methyl]-cyclohexyl}-benzamide
(anti,anti)-N-{2-[(2-chloro-phenyl)-dimethylamino-methyl]-cyclohexyl}-benzamide
(anti,anti)-N-{2-[dimethylamino-(2-methoxy-phenyl)-methyl]-cyclohexyl}-acetamide
(anti,anti)-2-[dimethylamino-(2-methoxy-phenyl)-methyl]-cyclohexylamine
(anti,anti)-N-{2-[(2-chloro-phenyl)-dimethylamino-methyl]-cyclohexyl}-acetamide
(anti,anti)-2-[(2-chloro-phenyl)-dimethylamino-methyl]-cyclohexylamine
(anti,anti)-N-{2-[dimethylamino-(2-nitro-phenyl)-methyl]-cyclohexyl}-acetamide
(anti,anti)-2-[dimethylamino-(2-nitro-phenyl)-methyl]-cyclohexylamine
(syn,syn)-2-(dimethylamino-phenyl-methyl)-cyclohexylamine
(syn,syn)-2-[(2-chloro-phenyl)-dimethylamino-methyl]-cyclohexylamine
(syn,anti)-2-(dimethylamino-phenyl-methyl)-cyclohexyl-N-(n-propyl)-amine
(syn,anti)-2-(dimethylamino-phenyl-methyl)-cyclohexyl-N-benzylamine
(syn,anti)-2-(dimethylamino-phenyl-methyl)-cyclohexylamine
(syn,anti)-2-[(2-chlorophenyl)-dimethylamino-methyl]-cyclohexylamine
(anti,anti)-2-[(2-chlorophenyl)-dimethylamino-methyl]-cyclohexylamine
(syn,syn)-2-(dimethylamino-phenyl-methyl)-cyclohexylamine
(anti,anti)-2-(dimethylamino-phenyl-methyl)-cyclohexylamine
(syn,syn)-2-[(2-chlorophenyl)-dimethylamino-methyl]-cyclohexylamine
(syn,syn)-2-(dimethylamino-pyridin-3-yl-methyl)-cyclohexylamine
(anti,anti)-2-(dimethylamino-pyridin-3-yl-methyl)-cyclohexylamine
(syn,syn)-2-(dimethylamino-(2-methoxyphenyl)-methyl)-cyclohexylamine
(anti,anti)-2-(dimethylamino-(2-methoxyphenyl)-methyl)-cyclohexylamine
(syn,syn)-2-(dimethylamino-(2-nitrophenyl)-methyl)-cyclohexylamine and
(anti,anti)-2-(dimethylamino-(2-nitrophenyl)-methyl)-cyclohexylamine.

14. A method for preparing a compound corresponding to claim 1 corresponding to formula (I)

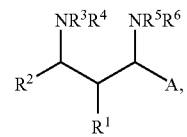

or a pharmaceutically acceptable salt thereof,
wherein
$R^1$ and $R^2$ together are —$(CH_2)_m$— and form a ring in combination with the carbons to which $R^1$ and $R^2$ are connected in formula (I), where m=2, 3, 4, 5 or 6, wherein the —$(CH_2)_m$— ring is optionally substituted one or more times by $C_{1-6}$-alkyl, aryl, O—$C_{1-6}$-alkyl, O—$(C_{1-6}$-alkyl)-aryl, or benzo-fused;
$R^3$ is selected from the group consisting of H, $C_{1-12}$-alkyl, $C_{3-8}$-cycloalkyl, aryl, —$(C_{1-6}$-alkyl)-$C_{3-8}$-cycloalkyl, —$(C_{1-6}$-alkyl)-aryl, heterocyclyl, and —$(C_{1-6}$-alkyl)-heterocyclyl,
$R^4$ is H;
$R^5$ and $R^6$ are independently selected from the group consisting of $C_{1-12}$-alkyl, $C_{3-8}$-cycloalkyl, —$(C_{1-6}$-alkyl)-$C_{3-8}$-cycloalkyl, aryl, and $(C_{1-6}$-alkyl)-aryl,
A is selected from the group consisting of aryl, heteroaryl, C(=O)O$R^{10}$, and 2-propyl;
wherein
$R^{10}$ is selected from the group consisting of $C_{1-6}$-alkyl, aryl, and —$(C_{1-6}$-alkyl)-aryl;
wherein the method comprises reacting an imine corresponding to formula (II) wherein $R^1$, $R^2$, $R^3$, $R^5$, $R^6$, and A have the meanings given above

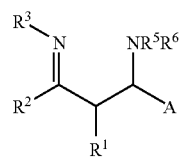

with a reducing agent.

15. The method of claim 14, wherein the reducing agent is a complex hydride.

16. The method of claim 14, wherein the method comprises diastereoselective preparation of a compound corresponding to formula (anti,anti-I)

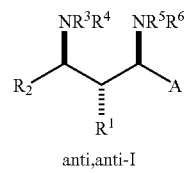

or a pharmaceutically acceptable salt thereof, wherein said imine of formula (II) is an imine of formula (anti-II)

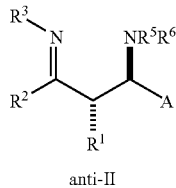

anti-II and the reducing is carried out in an alcoholic solvent.

17. The method of claim 16, wherein the reducing agent is selected from the group consisting of zinc cyanoborohydride ($ZnCNBH_3$), $LiBH_4$, $NaBH_4$, $NaBH_3CN$ and $NaBH(OC(=O)CH_3)_3$.

18. The method of claim 16, wherein the alcoholic solvent is methanol, and wherein reducing is carried out with warming from 0° C. to room temperature over 8 to 24 hours.

19. The method of claim 18, wherein the reducing is carried out with warming from 0° C. to room temperature over 10 to 14 hours.

20. The method of claim 14, wherein the method comprises diastereoselective preparation of a compound corresponding to structure (syn,syn-I)

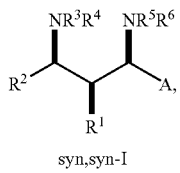

syn,syn-I or a pharmaceutically acceptable salt thereof,
wherein said imine corresponding to formula (II) is an imine corresponding to formula (anti-II)

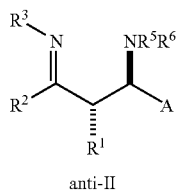

anti-II and the reducing is carried out in an ethereal solvent.

21. The method of claim 20, wherein the reducing agent is L-Selectride or diisobutylaluminum hydride.

22. The method of claim 20, wherein the ethereal solvent is tetrahydrofuran, and wherein the reducing is carried out with warming from 0° C. to room temperature over 8 to 24 hours.

23. The method of claim 22, wherein the reducing is carried out with warming from 0° C. to room temperature over 10 to 14 hours.

24. The process of claim 14, further comprising preparing the imine corresponding to formula (II) by reacting a Mannich base (III)

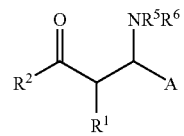

III with ammonium acetate when $R^3$ in structure (II) is H, or with an amine of the formula $R^3NH_2$ when $R^3$ is not H, in an ethereal or alcoholic solvent.

25. The process of claim 24, wherein said imine corresponding to formula (II) is an imine corresponding to formula (anti-II) and said Mannich base (III) is a Mannich base corresponding to formula (anti-III)

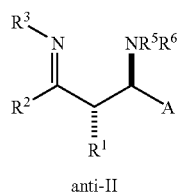 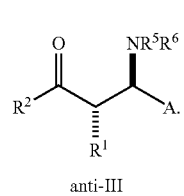

anti-II anti-III

26. A method for preparing a compound corresponding to formula (I)

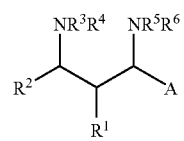

I or a pharmaceutically acceptable salt thereof,
wherein
$R^1$ and $R^2$ together are —$(CH_2)_m$— and form a ring in combination with the carbons to which $R^1$ and $R^2$ are connected in formula (I), where m=2, 3, 4, 5 or 6, wherein the —$(CH_2)_m$— ring is optionally substituted one or more times by $C_{1-6}$-alkyl, aryl, O—$C_{1-6}$-alkyl, O—($C_{1-6}$-alkyl)-aryl, or benzo-fused;
$R^3$ and $R^4$ are H;
$R^5$ and $R^6$ are independently selected from the group consisting of $C_{1-12}$-alkyl, $C_{3-8}$-cycloalkyl, —($C_{1-6}$-alkyl)-$C_{3-8}$-cycloalkyl, aryl, and ($C_{1-6}$-alkyl)-aryl;
A is selected from the group consisting of aryl, heteroaryl, $C(=O)OR^{10}$, or 2-propyl;
wherein
$R^{10}$ is selected from the group consisting of $C_{1-6}$-alkyl, $C_{3-8}$-cycloalkyl, —($C_{1-6}$-alkyl)-$C_{3-8}$-cycloalkyl, aryl, and —($C_{1-6}$-alkyl)-aryl;
wherein the method comprises:
(a) converting an amino-alcohol corresponding to formula (IV)

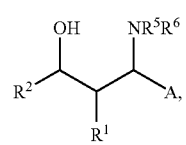

IV wherein $R^1$, $R^2$, $R^5$, $R^6$, and A have the meanings given above, into a compound corresponding to formula (V)

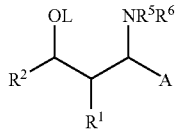

V wherein wherein $R^1$, $R^2$, $R^5$, $R^6$, and A have the meanings given above and L is mesyl or tosyl;

(b) converting the compound corresponding to formula (V) into an azide corresponding to formula (VI)

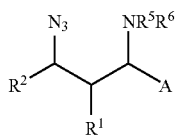

VI wherein $R^1$, $R^2$, $R^5$, $R^6$, and A have the meanings given above, and (c) reducing the azide corresponding to formula (VI) to a diamine corresponding to formula (I).

27. The method of claim 26, wherein converting the amino-alcohol corresponding to formula (IV) into a compound corresponding to formula (V) comprises reacting the compound corresponding to formula (IV) with mesyl chloride or tosyl chloride in the presence of a base.

28. The method of claim 26, wherein converting the compound corresponding to formula (V) to an azide corresponding to formula (VI) comprises reacting the compound corresponding to formula (V) with sodium azide.

29. The method of claim 26, wherein preparing the compound corresponding to formula (I) comprises diastereoselective preparation of a compound corresponding to formula (syn,anti-I) or (anti,anti-I)

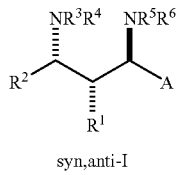 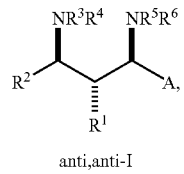

syn,anti-I      anti,anti-I or a pharmaceutically acceptable salt thereof;

wherein the amino-alcohol corresponding to formula (IV) is an amino-alcohol corresponding to formula (anti, anti-IV) or (syn,anti-IV)

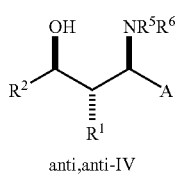 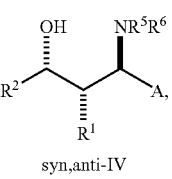

anti,anti-IV      syn,anti-IV the compound corresponding to formula (V) is a compound corresponding to formula (anti,anti-V) or (syn, anti-V)

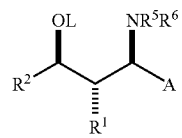 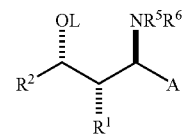

anti,anti-V      syn,anti-V wherein L denotes mesyl or tosyl;

and the azide corresponding to formula (VI) is an azide corresponding to formula (syn,anti-VI) or (anti,anti-VI)

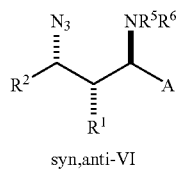 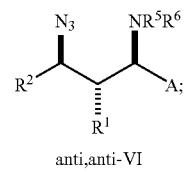

syn,anti-VI      anti,anti-VI

30. A method for preparing a compound according to claim 5 corresponding to formula (syn,anti-I)

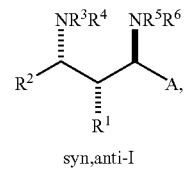

syn,anti-I or a pharmaceutically acceptable salt thereof, wherein $R^1$ and $R^2$ together are —$(CH_2)_m$— and form a ring in combination with the carbons to which $R^1$ and $R^2$ are connected in formula (I), where m=2, 3, 4, 5 or 6, wherein the —$(CH_2)_m$— ring is unsubstituted or monosubstituted or polysubstituted by $C_{1-6}$-alkyl, aryl, O—$C_{1-6}$-alkyl, O—$(C_{1-6}$-alkyl)-aryl, or benzo-fused;

$R^3$ is selected from the group consisting of H, $C_{1-12}$-alkyl, $C_{3-8}$-cycloalkyl, —$(C_{1-6}$-alkyl)-$C_{3-8}$-cycloalkyl, aryl, —$(C_{1-6}$-alkyl)-aryl, heterocyclyl and —$(C_{1-6}$-alkyl)-heterocyclyl;

$R^4$ is H;

$R^5$ and $R^6$ are independently selected from the group consisting of $C_{1-12}$-alkyl, $C_{3-8}$-cycloalkyl, —$(C_{1-6}$-alkyl)-$C_{3-8}$-cycloalkyl, aryl, and $(C_{1-6}$-alkyl)-aryl, A is selected from the group consisting of aryl, heteroaryl, C(=O)$OR^{10}$, and 2-propyl;

wherein $R^{10}$ is selected from the group consisting of $C_{1-6}$-alkyl, $C_{3-8}$-cycloalkyl, —$(C_{1-6}$-alkyl)-$C_{3-8}$-cycloalkyl, aryl, and —$(C_{1-6}$-alkyl)-aryl;

wherein the method comprises
(aa) reacting an imine corresponding to structure (VII)

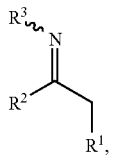

VII wherein $R^1$, $R^2$, and $R^3$ have the meanings give above, with an iminium salt corresponding to structure (VIII)

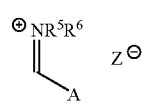

VIII wherein $R^1$, $R^2$, $R^5$, $R^6$, and A have the meanings given above and Z— is a suitable counter-ion to obtain an addition product; and
(bb) reducing the addition product from (aa) to obtain the compound corresponding to formula (syn, anti-I).

31. The method of claim 30, wherein the method comprises preparing a compound corresponding to formula (syn,anti-I)

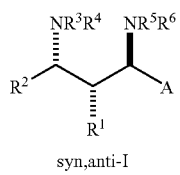

syn,anti-I wherein $R^1$, $R^2$, $R^4$, $R^5$, $R^6$, and A are as defined in claim 30 and $R^3$ is H, and wherein the process further comprises:
(cc) reacting a compound corresponding to formula (syn, anti-I), wherein $R^3$ is —(CH$_2$)-phenyl and where phenyl is unsubstituted or substituted by $C_{1-6}$-alkyl, with hydrogen (H$_2$) in the presence of a transition metal selected from the group consisting of platinum, palladium, and nickel.

32. A process for preparing a compound corresponding to formula (I)

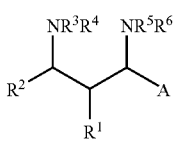

I or a pharmaceutically acceptable salt thereof,
wherein
$R^1$ and $R^2$ together are —(CH$_2$)$_m$— and form a ring in combination with the carbons to which $R^1$ and $R^2$ are connected in formula (I), where m=2, 3, 4, 5 or 6, wherein the —(CH$_2$)$_m$— ring is unsubstituted or mono-substituted or polysubstituted by $C_{1-6}$-alkyl, aryl, O—$C_{1-6}$-alkyl, O—($C_{1-6}$-alkyl)-aryl, or benzo-fused;
$R^3$ is C(=O)—$R^7$;
$R^4$ is selected from the group consisting of H, $C_{1-12}$-alkyl, $C_{3-8}$-cycloalkyl, aryl-($C_{1-6}$-alkyl)-$C_{3-8}$-cycloalkyl, —($C_{1-6}$-alkyl)-aryl, heterocyclyl, and —($C_{1-6}$-alkyl)-heterocyclyl;
$R^5$ and $R^6$ are independently selected from the group consisting of $C_{1-12}$-alkyl, $C_{3-8}$-cycloalkyl, —($C_{1-6}$-alkyl)-$C_{3-8}$-cycloalkyl, aryl, and ($C_{1-6}$-alkyl)-aryl, and
A is selected from the group consisting of aryl, heteroaryl, C(=O)O$R^{10}$, and 2-propyl;
wherein
$R^7$ is selected from the group consisting of $C_{1-6}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl, and —($C_{1-6}$-alkyl)-heterocyclyl;
$R^{10}$ is selected from the group consisting of $C_{1-6}$-alkyl, $C_{3-8}$-cycloalkyl, —($C_{1-6}$-alkyl)-$C_{3-8}$-cycloalkyl, aryl and —($C_{1-6}$-alkyl)-aryl;
wherein the prepared compound is present as a racemate or in the form of one or more diastereomers or one or more enantiomers, wherein the method comprises
reacting a compound corresponding to formula (I), wherein $R^3$ is H and $R^1$, $R^2$, $R^4$, $R^5$, and $R^6$ are as defined above, with an acylating reagent.

33. The process of claim 32, wherein the acylating reagent is an acid chloride of the formula $R^7$—C(=O)—Cl, wherein $R^7$ is selected from the group consisting of $C_{1-6}$-alkyl, aryl, —($C_{1-6}$-alkyl)-aryl, heterocyclyl, and —($C_{1-6}$-alkyl)-heterocyclyl.

34. A pharmaceutical composition comprising a compound corresponding to formula (I)

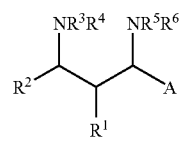

I or a pharmaceutically acceptable salt thereof, which is present as a racemate or in the form of one or more diastereomers or one or more enantiomers, and a pharmaceutically acceptable carrier or adjuvant,
wherein in formula (I)
$R^1$ and $R^2$ together are —(CH$_2$)$_m$— and form a ring in combination with the carbons to which $R^1$ and $R^2$ are connected in formula (I), where m=2, 3, 4, 5 or 6, wherein the —(CH$_2$)$_m$— ring is optionally substituted one or more times by $C_{1-6}$-alkyl, aryl, O—$C_{1-6}$-alkyl, O—($C_{1-6}$-alkyl)-aryl, or benzo-fused;
$R^3$ is selected from the group consisting of H, $C_{1-12}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl, —($C_{1-6}$-alkyl)-heterocyclyl, and C(=O)—$R^7$,
$R^4$ is selected from the group consisting of H, $C_{1-12}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl and —($C_{1-6}$-alkyl)-heterocyclyl,
$R^5$ and $R^6$ are independently selected from the group consisting of $C_{1-12}$-alkyl, $C_{3-8}$-cycloalkyl, —($C_{1-6}$-alkyl)-$C_{3-8}$-cycloalkyl, aryl, and ($C_{1-6}$-alkyl)-aryl,
A is selected from the group consisting of aryl, heteroaryl, C(=O)O$R^{10}$, and 2-propyl;

wherein
R$^7$ is selected from the group consisting of C$_{1-6}$-alkyl, C$_{3-8}$-cycloalkyl, —(C$_{1-6}$-alkyl)-C$_{3-8}$-cycloalkyl, aryl, —(C$_{1-6}$-alkyl)-aryl, heterocyclyl, and —(C$_{1-6}$-alkyl)-heterocyclyl;

R$^{10}$ is selected from the group consisting of C$_{1-6}$-alkyl, C$_{3-8}$-cycloalkyl, —(C$_{1-6}$-alkyl)-C$_{3-8}$-cycloalkyl, aryl, and —(C$_{1-6}$-alkyl)-aryl.

35. A method for treating pain in a mammal comprising administering a therapeutically effective amount of a compound corresponding to formula (I)

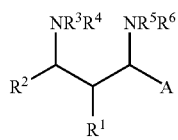

I or a pharmaceutically acceptable salt thereof, which is present as a racemate or in the form of one or more diastereomers or one or more enantiomers, wherein
R$^1$ and R$^2$ together are —(CH$_2$)$_m$— and form a ring in combination with the carbons to which R$^1$ and R$^2$ are connected in formula (I), where m=2, 3, 4, 5 or 6, wherein the —(CH$_2$)$_m$— ring is unsubstituted or monosubstituted or polysubstituted by C$_{1-6}$-alkyl, aryl, O—C$_{1-6}$-alkyl, O—(C$_{1-6}$-alkyl)-aryl, or benzo-fused;

R$^3$ is selected from the group consisting of H, C$_{1-12}$-alkyl, C$_{3-8}$-cycloalkyl, —(C$_{1-6}$-alkyl)-C$_{3-8}$-cycloalkyl, aryl, —(C$_{1-6}$-alkyl)-aryl, heterocyclyl, —(C$_{1-6}$-alkyl)-heterocyclyl, and C(=O)—R$^7$, R$^4$ is selected from the group consisting of H, C$_{1-12}$-alkyl, C$_{3-8}$-cycloalkyl, —(C$_{1-6}$-alkyl)-C$_{3-8}$-cycloalkyl, aryl, —(C$_{1-6}$-alkyl)-aryl, heterocyclyl and —(C$_{1-6}$-alkyl)-heterocyclyl, R$^5$ and R6 are independently selected from the group consisting of C$_{1-12}$-alkyl, C$_{3-8}$-cycloalkyl, —(C$_{1-6}$-alkyl)-C$_{3-8}$-cycloalkyl, aryl, and (C$_{1-6}$-alkyl)-aryl, A is selected from the group consisting of aryl, heteroaryl, C(=O)OR$^{10}$, and 2-propyl;

wherein
R$^7$ is selected from the group consisting of C$_{1-6}$-alkyl, C$_{3-8}$-cycloalkyl, —(C$_{1-6}$-alkyl)-C$_{3-8}$-cycloalkyl, aryl, —(C$_{1-6}$-alkyl)-aryl, heterocyclyl and —(C$_{1-6}$-alkyl)-heterocyclyl;

R$^{10}$ is selected from the group consisting of C$_{1-6}$-alkyl, C$_{3-8}$-cycloalkyl, —(C$_{1-6}$-alkyl)-C$_{3-8}$-cycloalkyl, aryl, and —(C$_{1-6}$-alkyl)-aryl.

* * * * *